United States Patent [19]
Denoya

[11] Patent Number: 5,728,561
[45] Date of Patent: Mar. 17, 1998

[54] **GENES ENCODING BRANCHED-CHAIN ALPHA-KETOACID DEHYDROGENASE COMPLEX FROM *STREPTOMYCES AVERMITILIS***

[75] Inventor: Claudio D. Denoya, Groton, Conn.

[73] Assignee: Pfizer Inc., New York, N.Y.

[21] Appl. No.: 482,385

[22] Filed: Jun. 7, 1995

Related U.S. Application Data

[62] Division of Ser. No. 432,330, May 1, 1995, which is a continuation of Ser. No. 100,518, Jul. 30, 1993, abandoned.

[51] Int. Cl.$^6$ ............................................. C12N 9/04
[52] U.S. Cl. ............................................................ 435/190
[58] Field of Search ................... 536/23.2, 2; 435/240.2, 435/252.3, 190, 252.33; 530/324, 350

[56] References Cited

FOREIGN PATENT DOCUMENTS 0284176   1/1988   European Pat. Off. .

OTHER PUBLICATIONS

Wexler et al. 1991 Febs Lett. 282(1) 209–213.

Ovnic et al. 1991 Genomics 11 pp. 956–967.

*Primary Examiner*—James Ketter
*Assistant Examiner*—Irem Yucel
*Attorney, Agent, or Firm*—Peter C. Richardson; Gregg C. Benson; Robert F. Sheyka

[57] ABSTRACT

The present invention relates to novel DNA sequences that encode for the branched-chain alpha-ketoacid dehydrogenase complex of an organism belonging to the genus Streptomyces and to novel polypeptides produced by the expression of such sequences. It also relates to novel methods of enhancing the production of natural avermectin and of producing novel avermectin through fermentation.

2 Claims, 15 Drawing Sheets

FIG. 1A

```
            G   D   G   A   T   S   E   G   D
▷  5'-GAATTCGGCGACGGCGCCACCTCCGAGGGCGAC-3'
       EcoRI
```

FIG. 1B

```
        E   M   P   D   H   L   R
   5'-GAGATGCCGGACCACCTGCGG-3'
   3'-CTCTACGGCCTGGTGGACGCCAGATCT-5'  ◁
                                  XbaI
```

FIG. 2

```
Sa  DGATSEGDFHEALNFAAVWQAPVVFLVQNNGFAISV.PLAKQTAAPSLAQKAVGYEMPDHLR
Bs  DGGTSQGDFYEGINFAGAFKAPAIFVVQNNRFAIST.PVEKQTVAKTLAQKAVAAGIPG.IQ
Pp  DGATAESDFHTALTFAHVYRAPVILNVVNNQWAISTFQAIAGGESTTFAGRGVGCGIAS.LR
Hs  EGAASEGDAHAGFNFAATLECPIIFFCRNNGYAIST.PTSEQYRGDGIAARGPGYGIMS.IR
```

FIG. 4A

```
        10         20         30         40         50         60         70
GTCGACGCGG GCTCCGAAAC CGCGGATCAC GCCGTCGTCG ATGAGCCGGT TGATTCCGCG GTAGGCATTG 80         90        100        110        120        130        140
GCACGCGACA CGTGGGGCGCG CTCGGCCACG GACCGTATCG AGGCGCGGCC GTCCGCCTGG AGCATCTGGA 150        160        170        180        190        200        210
GGATGTCCTG ATCGATGGCG TCCAGCGGGC GGGCGGGGCGG CAGGGGTACC CCGGGCTCCG CTCCCTCGGC 220        230        240        250        260        270        280
CATTTGTTCA GGTGCCATGT CCTCCGGCCT CCTTACCATG GACGTAGTGC GTTCATTCCA GGCTGTGGAG 290        300        310        320        330        340        350
AACCGTTTGT CCACAGCCTG ACGGTGCCTG TAGCCAAAAT GTGCCGACGA CCGAACAATC GGTAGGTGAG
```

FIG. 4B

```
     360        370        380        390        400             411
GCGCCTCACA CCCGTGGCGC GCCCAAAGCC GCTCCCACGA GGAGGTGCCG TC ATG ACG GTC
                                                         M   T   V 420        429        438        447        456             465
ATG GAG CGG GGC GCT TAC CGG CCC ACA CCG CCC GCC TGG CAG CCC CGC
 M   E   R   G   A   Y   R   P   T   P   P   A   W   Q   P   R 474        483        492        501        510             519
ACC GAC GCG CCA CTG CTG CCC GAC CCC CAC CGC GCC CTG GTC GGC ACC
 T   D   A   P   L   L   P   D   P   H   R   A   L   V   G   T 528        537        546        555        564             573
GAG GCG GCG GAG CCC GCG CTA CTG GAC CTG CTG CGC CGC CTG TAC GCG
 E   A   A   E   P   A   L   L   D   L   L   R   R   L   Y   A 582        591        600        609        618             627
GTG CGC CGC TAC AAC ACG CAG GCC ACG GCT CTC ACC AAG CAG GGC CGG
 V   R   R   Y   N   T   Q   A   T   A   L   T   K   Q   G   R
```

FIG. 4C

| Pos | Codon | AA | Codon | AA | Codon | AA | Codon | AA | Codon | AA | Codon | AA |
|-----|-------|----|----|----|----|----|----|----|----|----|----|----|
| 636 | CTC | L | GCC | A | GTC | V | TAC | Y | CCG | P | | |
| 645 | TCG | S | AGC | S | ACG | T | GGC | G | | | | |
| 654 | CAG | Q | GAG | E | GCC | A | | | | | | |
| 663 | TGC | C | GCC | A | GCC | A | | | | | | |
| 672 | GTC | V | GCC | A | GCG | A | | | | | | |
| 681 | | | | | | | | | | | | |
| | CTC | L | GTG | V | CTG | L | GAG | E | GAG | E | | |
| 699 | CGC | R | GAC | D | TGG | W | | | | | | |
| 708 | CTC | L | TTC | F | CCC | P | | | | | | |
| 717 | AGC | S | TAC | Y | GCC | A | | | | | | |
| 726 | ACC | T | CTC | L | GCC | A | | | | | | |
| 735 | | | | | | | | | | | | |
| | GCC | A | CGC | R | GGC | G | TAC | Y | CGG | R | | |
| 753 | CTC | L | GAT | D | CCC | P | | | | | | |
| 762 | CAG | Q | GCG | A | GTC | V | | | | | | |
| 771 | CTC | L | ACC | T | CGC | R | | | | | | |
| 780 | CTG | L | CGC | R | GCC | A | | | | | | |
| 789 | | | | | | | | | | | | |
| | GCC | A | GTC | V | CGT | R | GAT | D | CCC | P | | |
| 807 | CTC | L | ACC | T | GCG | A | | | | | | |
| 816 | GTC | V | CAG | Q | GCG | A | | | | | | |
| 825 | CTC | L | ACC | T | ATC | I | | | | | | |
| 834 | CTG | L | TGC | C | ACC | T | | | | | | |
| 843 | | | | | | | | | | | | |
| | TGG | W | CAC | H | TAC | Y | GAC | D | GAG | E | | |
| 861 | CCG | P | CTC | L | CAG | Q | | | | | | |
| 870 | GTC | V | GGC | G | CAC | H | | | | | | |
| 879 | ATC | I | CGC | R | GAG | E | | | | | | |
| 888 | GCC | A | CCC | P | CGC | R | | | | | | |
| 897 | | | | | | | | | | | | |
| | CTC | L | GCG | A | CAG | Q | CTC | L | CCG | P | | |
| | ACC | T | CAG | Q | CTC | L | CAC | H | CCT | P | | |
| | GCG | A | GCC | A | GGC | G | CGC | R | ACC | T | | |
| | CTC | L | GCC | A | CTC | L | CGC | R | AAG | K | | |

FIG. 4D

| Pos | Codons (5'→3') and amino acids |
|---|---|
| 906 | GGC GAC GTG GTC GCG CTC GCC CTG GGC GAC GGC AGC GAG GGC |
|  | G   D   V   V   A   L   A   L   G   D   G   S   E   G  |
| 960 | GAC TTC CAC GAG GCA AAC GGC TTC GCC GTC GGC GAC TGG TTC |
|  | D   F   H   E   A   N   G   F   A   V   G   D   W   F  |
| 1014 | CTC GTG CAG AAC CTG AAC TTC GCC ATC TCC GTC CCG CAG GCG |
|  | L   V   Q   N   L   N   F   A   I   S   V   P   Q   A  |
| 1068 | GCC CCG TCG CTG GCC CAC AAG GCC TTC GCC AAG GGC GCC CTC |
|  | A   P   S   L   A   H   K   A   F   A   K   G   A   L  |
| 1122 | GAC AAC GAC GCA GCG GCC GTC GAG GGG TAC GGC CCG ATG CCG |
|  | D   N   D   A   A   A   V   E   G   Y   G   P   M   P  |
|  |  G   R   A |

Reading columns left-to-right with position markers: 906, 915, 924, 933, 942, 951 / 960, 969, 978, 987, 996, 1005 / 1014, 1023, 1032, 1041, 1050, 1059 / 1068, 1077, 1086, 1095, 1104, 1113 / 1122, 1131, 1140, 1149, 1158, 1167

Full sequence readout:

- 906: GGC(G) GAC(D) GTG(V) — 915: GTC(V) GCG(A) CTC(L) — 924: GCC(A) CTG(L) GGC(G) — 933: GAC(D) GGC(G) AGC(S) — 942: GAG(E) GGC(G) [951]
- 960: GAC(D) TTC(F) CAC(H) — 969: GAG(E) GCA(A) AAC(N) — 978: GGC(G) TTC(F) GCC(A) — 987: GTC(V) GGC(G) GAC(D) — 996: TGG(W) TTC(F) [1005]
- 1014: CTC(L) GTG(V) CAG(Q) — 1023: AAC(N) CTG(L) AAC(N) — 1032: TTC(F) GCC(A) ATC(I) — 1041: TCC(S) GTC(V) CCG(P) — 1050: CAG(Q) GCG(A) [1059]
- 1068: GCC(A) CCG(P) TCG(S) — 1077: CTG(L) GCC(A) CAC(H) — 1086: AAG(K) GCC(A) TTC(F) — 1095: GCC(A) AAG(K) GGC(G) — 1104: GCC(A) CTC(L) [1113]
- 1122: GAC(D) AAC(N) GAC(D) — 1131: GCA(A) GCG(A) GCC(A) — 1140: GTC(V) GAG(E) CAC(H) — 1149: GGG(G) TAC(Y) CTC(L) — 1158: AGC(S) GTG(V) GCC(A) — 1167: CAC(H)

FIG. 4E

```
                         1176            1185            1194            1203            1212            1221
GCC  GCG  CGC  GGA  GGG  CGC  ACG  CCG  ACG  CTC  GTG  GAG  GCG  ACC  TAC  CGC  ATC  GAC
 A    A    R    G    G    R    T    P    T    L    V    E    A    T    Y    R    I    D 1230            1239            1248            1257            1266            1275
GCC  CAC  AAC  GCC  GAC  ACG  CGC  TAC  GCG  ACG  GAC  GCC  GGG  TCC  GAG  GAG  GTG  GAG
 A    H    N    A    D    T    R    Y    A    T    D    A    G    S    E    E    V    E 1284            1293            1302            1311            1320            1329
GCC  ACC  GAC  GAG  CAC  GAC  CCG  ATC  GCG  CTC  GAG  CGG  TAC  GGG  GAG  CAC  ACC  GAG
 A    T    D    E    H    D    P    I    A    L    E    R    Y    G    E    H    T    E 1338            1347            1356            1365            1374            1383
GGG  CTC  CGC  GCG  GAC  GGC  ATC  GCG  CGG  GCC  GCC  CGC  GAG  GAC  GAG  TTG  ACC  GAA
 G    L    R    A    D    G    I    A    R    A    A    R    E    D    E    L    T    E 1392            1401            1410            1419            1428            1437
GCC  GAC  CTG  CGC  GCA  CGC  ATG  AAC  CAG  GAT  CCG  GCC  CTG  GAC  CCC  ATG  GCG  GAC
 A    D    L    R    A    R    M    N    Q    D    P    A    L    D    P    M    A    D
```

FIG. 4F

```
       1446              1455              1464              1473              1482              1491
CTG    TTC    GCC    CAT    GTG    TAT    GCC    GAG    CCC    ACC    CCC    CAG    CTG    CGG    GAG    CAG    GAA    GCC
 L      F      A      H      V      Y      A      E      P      T      P      Q      L      R      E      Q      E      A 1500              1509              1518              1527              1536              1545
CAG    TTG    CGG    GCC    GAG    GCG    GCA    GAG    GCC    GAC    GGG    CCC    CAA    GGA    GTC    GGC    CGA
 Q      L      R      A      E      A      A      E      A      D      G      P      Q      G      V      G      R 1558              1568              1578              1588              1598              1608
TGA    AGAGAGTTGA    CCATCGGGCC    CCGAGAAGCG    GGCCGATGAC    CTCCGTTGGC    CTTTGGCCGG
 *

1618              1627              1636              1645              1654              1663
AAGGAGCCGG    GCG    ATG    ACC    ACC    GTT    GCC    CTC    AAG    CCG    GCC    ACC    ATG    GCG    CAG    GCA
              A      M      T      T      V      A      L      K      P      A      T      M      A      Q      A 1672              1681              1690              1699              1708              1717
CTC    ACA    CGC    GCG    GCG    TTG    CGT    GAC    GCC    ATG    GCC    GAC    CCC    GCC    GTC    CAC    GTG    ATG
 L      T      R      A      A      L      R      D      A      M      A      D      P      A      V      H      V      M
```

FIG. 4G

```
                    1726      1735      1744      1753      1762      1771
GGC  GAG  GAC  GTC  GGC  ACG  CTC  GGC  GTC  TTC  CGG  GTC  ACC  GAC  GGG  CTC  GCC
 G    E    D    V    G    T    L    G    V    F    R    V    T    D    G    L    A 1780      1789      1798      1807      1816      1825
AAG  GAG  TTC  GGC  GAG  GAC  CGC  TGC  ACG  GAC  ACG  CCG  CTC  GCC  GAG  GCA  ATC
 K    E    F    G    E    D    R    C    T    D    T    P    L    A    E    A    I 1834      1843      1852      1861      1870      1879
CTC  GGC  ACG  GCC  GTC  GGC  ATG  TAC  GGG  CTG  CTC  GCC  GTC  CAT  GAG  ATG
 L    G    T    A    V    G    M    Y    G    L    L    A    V    H    E    M 1888      1897      1906      1915      1924      1933
CAG  TTC  GAC  GCG  TTC  GCG  TAC  CCG  GGG  TTC  GAG  CAG  CTC  ATC  AGC  GGC  ATG
 Q    F    D    A    F    A    Y    P    G    F    E    Q    L    I    S    G    M 1942      1951      1960      1969      1978      1987
CGG  GAT  GCG  CAA  CGC  ACC  GGG  GCG  ATG  CCG  CTG  CCG  ATC  ACC  CAT  GTC  CGT  GTC
 R    D    A    Q    R    T    G    A    M    P    L    P    I    T    H    V    R    V
```

FIG. 4H

```
1996           2005           2014           2023           2032           2041
CCC TAC GGC    GGA ATC GGC    GGA GTC GAA    CAC AGC GAC    TCC GAG GCG
 P   Y   G      G   I   G      G   V   E      H   S   D      S   E   A 2050           2059           2068           2077           2086           2095
TAC TAC ATG    GCG ACT CCG    GGG CTC CAT    GTC GAA CAC    TCC ACG GTC    GCC GAC
 Y   Y   M      A   T   P      G   L   H      V   E   H      S   T   V      A   D 2104           2113           2122           2131           2140           2149
GCG TAC GGG    CTG CTG CGC    GCC GCC ATC    GAC GAC CCC    GCC GTC ACG    TTC CTG
 A   Y   G      L   L   R      A   A   I      D   D   P      A   V   T      F   L 2158           2167           2176           2185           2194           2203
GAG CCC AAG    CGG CTG TAC    TGG TCG GCC    TCC TGG AAC    CCG GAC GTC    GAG CCG GGG
 E   P   K      R   L   Y      W   S   A      S   W   N      P   D   V      E   P   G 2212           2221           2230           2239           2248           2257
GCG TAC ATA    GGC CGG GTG    GCG GTG CGG    CGC CGC TCG    GGC CGG GAG    CCG GGG
 A   Y   I      G   R   V      A   V   R      R   R   S      G   R   E      P   G

2257
ACC GTT GAA    CCG GCG GTG    CGC GCG GTG    GAC AAG TGG    TCC TGG AAC    AGC CGG GTG    GCC ACG
 T   V   E      P   A   V      R   A   V      D   K   W      S   W   N      S   R   V      A   T
```

FIG. 41

```
      2266            2275            2284            2293            2302            2311
CTC ATC ACG     TAC GGG CCT     TCC CTG CCC     GTC TGC CTG     GAG GCG GCC     GCG GCC
 L   I   T       Y   G   P       S   L   P       V   C   L       E   A   A       A   A 2320            2329            2338            2347            2356            2365
CGG GCC GAG     GGC TGG GAC     CTC GAA GTC     GAT CTG CGC     TCC CTG GAG     CCC TTC
 R   A   E       G   W   D       L   E   V       D   L   R       S   L   E       P   F 2374            2383            2392            2401            2410            2419
GAC GAG ACG     GTT GTG CGC     CGC GTG GGT     GCG CGG ACC     GGA CGC GAG     GTC GTG
 D   E   T       V   V   R       R   V   G       A   R   T       G   R   E       V   V 2428            2437            2446            2455            2464            2473
TCG GGT GGT     TAC GGC GTC     GGC CCG GGG     GAG GAG ATC     GCC GCG GCC     ATC ACC
 S   G   G       Y   G   V       G   P   G       E   E   I       A   A   A       I   T 2482            2491            2500            2509            2518            2527
TGC CAC CAT     TTC CAC CTG     GCG CCG GTG     CTG CGC GTC     GCC GTC CGC     GGG TTC GAC
 C   H   H       F   H   L       A   P   V       L   R   V       A   V   R       G   F   D
```

FIG. 4J

```
ATC CCG TAT CCG CCG ATG CTG GAG CGC CAT CTG CCC GGT GTC GAC CGG
 I   P   Y   P   P   M   L   E   R   H   L   P   G   V   D   R
2536        2545        2554        2563        2572        2581

ATC CTG GAC GCG GTG TTC AAG CTC CCC GAC CTT CAG TGG GAG GCG GGG AGC TG ATG GCC CAG
 I   L   D   A   V   F   K   L   P   D   L   Q   W   E   A   G   S   *   M   A   Q
2590        2599        2608        2617        2628

2637        2646        2655        2664        2673        2682
GTG CTC GAG TTC AAG CTC CCC GAC CTT CAG TGG GAG GGG GAG GGC CTG ACC GAG GCC GAG ATC
 V   L   E   F   K   L   P   D   L   Q   W   E   G   E   G   L   T   E   A   E   I 2691        2700        2709        2718        2727
GTC CGC TGG CTG GTG CAG GTC GAC GGC GTG GCG ATC G
 V   R   W   L   V   Q   V   D   G   V   A   I
```

FIG. 5

```
                                      11                  20                 29                 38               47
                    AG ATC TCC       CTC ATC       GCG CTG CTC       GCC AGG ATC       TGC ACC GCC       GCA CTG GCC       CGC
                       I   S          L   I         A   L   L         A   R   I         C   T   A         A   L   A         R 56                  65                 74                 83                 92                101
TTC CCC GAG         CTC AAC TCC       ACC GTC GAC       ATG GAC GCC       CGC GAG GTC       GTA CGG CTC
 F   P   E           L   N   S         T   V   D         M   D   A         R   E   V         V   R   L 110                 119                128                137                146                155
GAC CAG GTG         CAC CTG GGC       TTC GCC GAC       CAG ACC GAA       CGG GGG CTC       GTC GTC CCG
 D   Q   V           H   L   G         F   A   D         Q   T   E         R   G   L         V   V   P 164                 173                182                191                200                209
GTC GTG CGG         GAC GCG CAC       GCC CGG GAC       GCC GAG TCG       CTC AGC GCC       GAG TTC GCG
 V   V   R           D   A   H         A   R   D         A   E   S         L   S   A         E   F   A 218                 227                236                245
CGG CTG ACC         GAG GCC GCC       CGG GCC ACC       ACC CTC ACA
 R   L   T           E   A   A         R   A   T         T   L   T
```

FIG. 6A

```
                              M   T   V   M   E   Q   R
#55-PCR   ▷  5'-AAGAGATCTCATATGACGGTCATGGAGCAGCGG-3'
                 BglII NdeI
```

```
                              M   T   T   V   A   L   K
#56-PCR   ▷  5'-AAGAGATCTCATATGACCACCGTTGCCCTGAAG-3'
                 BglII NdeI
```

FIG. 6B

```
#30-BP-PCR  3'-AGCAAAATGTTGCAGCACTGAACCGACGTCCTAGGAA-5' ◁
                                         PstI BamHI
```

```
#31-BP-PCR  3'-ACCGCATTAGTACCAGTATCGACAGACGTCCTAGGAA-5' ◁
                                         PstI BamHI
```

GENES ENCODING BRANCHED-CHAIN ALPHA-KETOACID DEHYDROGENASE COMPLEX FROM *STREPTOMYCES AVERMITILIS*

This is a division of application Ser. No. 08/432,330, filed on May 1, 1995 which is a continuation of Ser. No. 08/100,518, filed Jul. 30, 1993, now abandoned.

BACKGROUND OF THE INVENTION

The present invention relates to novel DNA sequences that encode for the branched-chain alpha-ketoacid dehydrogenase complex of an organism belong to the genus Streptomyces and to novel polypeptides produced by the expression of such sequences. It also relates to novel methods of enhancing the production of natural avermectin and of producing novel avermectins through fermentation.

Numerous pharmaceutical products are produced by microorganisms. Among these microorganisms, members of the genus Streptomyces—a group of gram-positive soil bacteria—have received substantial attention having yielded more than 90% of the therapeutically useful antibiotics. Streptomycetes are the focus of intensive research applying recombinant DNA cloning techniques in order to isolate antibiotic biosynthetic genes, generate novel derivatives or hybrid compounds, isolate regulatory genes, and investigate the regulatory mechanisms involved in both primary and secondary metabolism.

*S. avermitilis* produces eight distinct but closely related antiparasitic polyketide compounds named avermectins. The avermectin complex produced by *S. avermitilis* has four major components, A1a, A2a, B1a, and B2a, and four minor components, A1b, A2b, B1b, and B2b. The structure of the various components are depicted below.

The avermectin polyketide structure is derived from seven acetate, five propionate molecules, and one alpha-branched-chain fatty acid molecule, which is either S(+)-2-methylbutyric acid or isobutyric acid. The designations "A" and "B" refer to avermectins wherein the 5-substituent is methoxy or hydroxy, respectively. The numeral "1" refers to avermectins wherein a double bond is present at the 22–23 position, and numeral "2" to avermectins having a hydrogen at the 22-position and hydroxy at the 23-position. Lastly, the C-25 has two possible substituents: the sec-butyl substituent (derived from L-isoleucine) is present in the avermectin "a" series, and the isopropyl substituent (derived from L-valine) is present in the avermecin "b" series (for a review see Fisher, M. H. and Mrozik, H., 1984, "Macrolide Antibiotics", Academic Press, chapter 14).

By "natural" avermectins is meant those avermectins produced by *S. avermitilis* wherein the 25-position substituent is, as mentioned above, either isopropyl or sec-butyl. Avermectins wherein the 25-position group is other than isopropyl or sec-butyl are referred to herein as novel or non-natural avermectins.

One metabolic route to these alpha-branched-chain fatty acids in their CoA form is through a branched-chain amino acid transaminase reaction followed by a branched-chain alpha-ketoacid dehydrogenase reaction. (Alternatively, branched-chain fatty acyl-CoA derivatives can arise from branched-chain alpha-ketoacids produced by de novo synthesis). These metabolic pathways are depicted below.

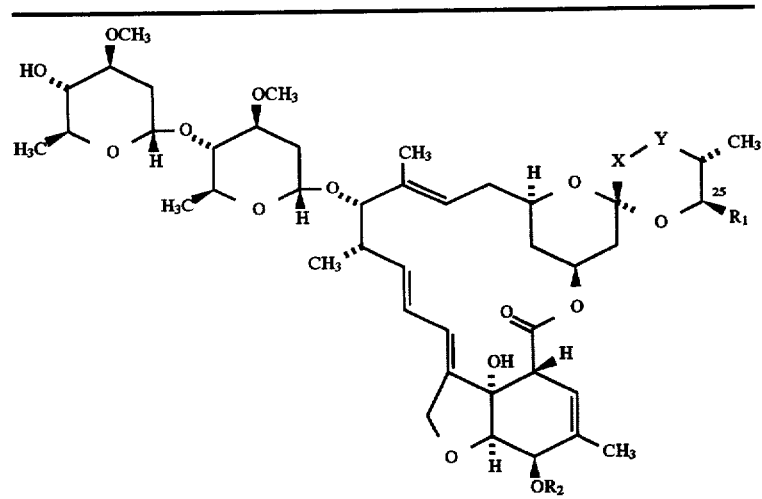

| Avermectin | R$^1$ | R$^2$ | X-Y |
|---|---|---|---|
| A1a | sec-butyl | Me | CH=CH |
| A1b | Isopropyl | Me | CH=CH |
| A2a | sec-butyl | Me | CH$_2$—CH(OH) |
| A2b | Isopropyl | Me | CH$_2$—CH(OH) |
| B1a | sec-butyl | H | CH=CH |
| B1b | Isopropyl | H | CH=CH |
| B2a | sec-butyl | H | CH$_2$—CH(OH) |
| B2b | Isopropyl | H | CH$_2$—CH(OH) |

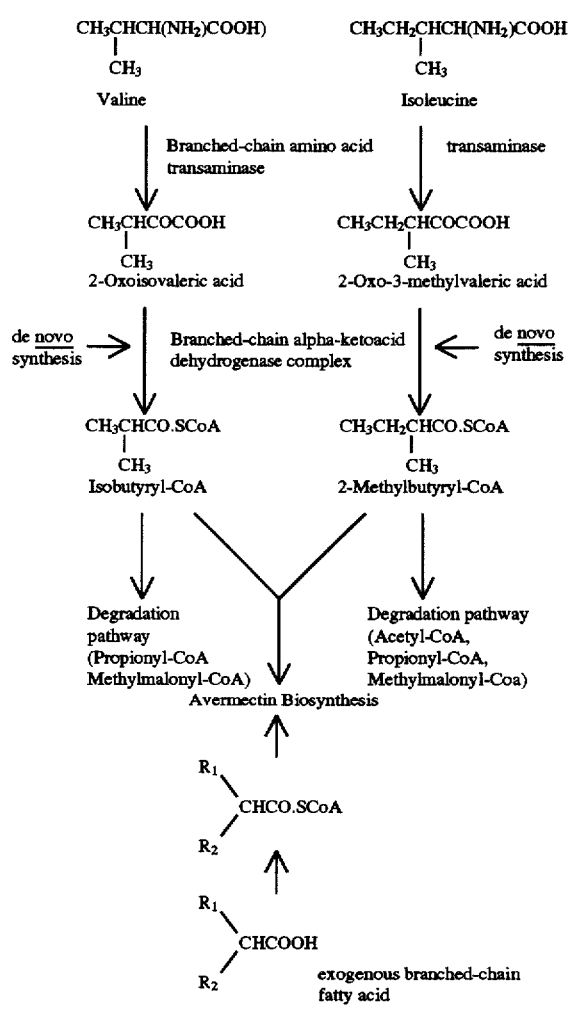

A mutant of S. avermitilis with no detectable branched-chain alpha-ketoacid dehydrogenase (BCKDH) activity in the last mentioned enzyme was previously isolated (Hafner et al., 1988, European Patent Application #88300353.5, publication #0 284176). The mutant was isolated following standard chemical mutagenesis of S. avermitilis strain ATCC 31272 in a screen searching for the absence of $^{14}CO_2$ production from $^{14}C$-1 labeled 2-oxoisocaproic acid substrate (leucine analog). The mutant is unable to synthesize natural avermectins except when the alpha-branched-chain fatty acid or a precursor bearing the isopropyl or sec-butyl (S-form) group is added to the medium in which the mutants are fermented. The mutant is also capable of producing novel or non-natural avermectins when fermented under aqueous aerobic conditions in a nutrient medium containing an appropriate alternative carboxylic acid, such as cyclohexane carboxylic acid (CHC), or a precursor thereof.

To clone S. avermitilis BCKDH is highly desirable. Manipulation of these genes through recombinant DNA techniques should facilitate the production of natural and novel avermectins. For certain strains, increased titer of natural avermectins would be anticipated by increasing the copy number of the BCKDH genes. In addition, generation of an irreversibly blocked bkd strain, having BCKDH activity permanently deleted or modified by gene replacement, would be an improved alternative to the current bkd mutant which was obtained, as mentioned before, by chemical mutagenesis.

The alpha-ketoacid dehydrogenase multienzyme complexes—the branched-chain alpha-ketoacid dehydrogenase (BCKDH) complex, the pyruvate dehydrogenase (PDH) complex, and the alpha-ketoglutarate dehydrogenase (KGDH) complex catalyze the oxidative decarboxylations of branched-chain alpha-ketoacids, pyruvate, and alpha-ketoglutarate, respectively, releasing CO2 and generating the corresponding Acyl-CoA and NADH (Perham, R. N., 1991, Biochemistry, 30: 8501-8512). Each complex consists of three different catalytic enzymes: decarboxylase (E1), dihydrolipoamide acyltransferase transacylase (E2), and dihydrolipoamide dehydrogenase (E3).

Branched-chain alpha-ketoacid dehydrogenase (BCKDH) is a multienzyme complex composed of three functional components, E1, the decarboxylase, E2, the transacylase, and E3, the lipoamide dehydrogenase. The purified complexes from Pseudomonas putida, Pseudomonas aeruqinosa, and Bacillus subtilis, are composed of four polypeptides. The purified mammalian complexes also consist of four polypeptides, E1alpha, E1beta, E2, and E3. An alpha-ketoacid dehydrogenase complex has been isolated from Bacillus subtills which has both pyruvate and branched-chain alpha-ketoacid dehydrogenase activities. This dual function complex oxidizes pyruvate and provides branched-chain fatty acids for membrane phospholipids.

Cloning of prokaryotic branched-chain alpha-ketoacid dehydrogenase genes has been reported for Pseudomonas and Bacillus, but not for Streptomyces. In these systems it was found that the genes encoding the BCKDH were clustered in an operon. The genes of the BCKDH complex of Pseudomonas putida have been cloned and the nucleotide sequence of this region determined (Sykes et al., 1987, J. Bacteriol., 169:1619–1625, and Burns et al., 1988, Eur. J. Biochem, 176:165–169, and 176:311–317). The molecular weight of E1alpha is 45289, of E1beta is 37138, of E2 is 45134, and of E3 is 48164. The four genes are clustered in the sequence: E1alpha, E1beta, E2, and E3. Northern blot analysis indicated that expression of these four genes occurs from a single mRNA and that these genes constitute an operon. There is a typical prokaryotic consensus promoter immediately preceding the start of the E1alpha coding region that permits the constitutive expression of the Pseudomonas bkd genes. The initiator codon for the E1beta coding region is located only 40 nucleotides downstream from the end of the E1alpha open reading frame (ORF). In contrast, there is no intergenic space between the E1beta and E2 ORFs since the stop codon for the E1beta ORF is the triplet immediate preceding the initiator codon of the E2 ORF. The intergenic space between the E2 and the E3 ORFs is reduced to only 2 nucleotides. Therefore, the Pseudomonas bkd genes are tightly linked. Similarly, the operon coding for the Bacuillus subtilis BCKDH/PDH dual complex has been cloned (Hemila et al., 1990, J. Bacteriol., 172:5052–5063). This operon contain four ORFs encoding four proteins of 42, 36, 48, and 50 kilodaltons (kDa) in size, shown to be highly homologous to the E1alpha, E1beta, E2, and E3 subunits of the Pseudomonas bkd cluster. Recently, the genes encoding the alpha and beta subunits of the E1component of the dual BCKDH/PDH multienzyme complex from Bacillus stearothermophilus were also cloned and sequenced (estimated molecular weights of the alpha and beta subunits are approximately 41,000 and 35,000, respectively) (Hawkins et al., 1990, Eur. J. Biochem., 191:337–346).

Additionally, the sequence of a number of eukaryotic E1alpha and beta BCKDH subunits (human, bovine, and rat) have been disclosed. Recently, an amino acid sequence comparison of all the published sequences known for both E1alpha and E1beta components of the PDH and the BCKDH complexes from multiple species was performed by computer analysis (Wexler et al., 1991, FEBS Letters, 282:209-213). Interestingly, several regions of the alpha and beta subunits were identified that are highly conserved not only in all PDHs so far described, but also in both prokaryotic and eukaryotic BCKDH complexes.

We describe the cloning of branched-chain alpha-ketoacid dehydrogenase genes from *Streptomyces avermitilis*. The novel genes were cloned using a combination of two molecular genetics techniques, DNA polymerase chain reaction (PCR) and homology probing. Homology probing involves screening cDNA or genomic libraries with radioactively-labeled synthetic oligonucleotide probes corresponding to amino acid sequences of the protein. Unfortunately, this technique has certain limitations, one of which is the further severe restriction on the degeneracy of the oligonucleotide that can be used. In addition, screening hybridization is performed at low stringency, so the number of false positives is often high. To overcome some of the limitations of oligonucleotide hybridization, a variation of homology probing that involves DNA polymerase chain reaction (PCR) and allows the use of highly degenerate oligonucleotides as probes was recently developed. This method requires only a knowledge of the amino acid sequence of two short regions (approximately 7-10 amino acids in length) of the encoded protein. Two oligonucleotides corresponding to each peptide sequence are used as primers in the reaction. Each primer can be used as a mixture of fully degenerate oligonucleotides containing all possible codon combinations that could encode the known amino acid sequences. The template for the amplification may be any of several DNA sources, including genomic DNA and supercoiled forms of plasmid libraries. Several reports, recently published in the literature, have demonstrated the usefulness of combining the polymerase chain reaction with homology probing for the identification of a gene from multiple species.

GLOSSARY

Technical terms used throughout this application are well known to those skilled in the art of molecular genetics. Definition of those terms are found in many textbooks dedicated to the molecular biology field, such as "Genes", Second Edition, by Dr. Benjamin Lewin, 1985, John Wiley & Sons, Inc. New York. Terms frequently used in this document are defined below:

Antibiotic: A chemical agent that inhibits growth of bacterial cells. Used to select recombinant bacterial cells.

Antibiotic Resistance Gene: DNA sequence that conveys resistance to antibiotic when introduced into a host cell that is naturally sensitive to that particular antibiotic. Also known as antibiotic marker.

Bacteriophages: Viruses that infect bacteria.

cRNA: Single-stranded RNA complementary to a DNA, synthesized from the latter by in vitro transcription.

Chromosome: Discrete unit of the genome carrying many genes.

Clone: Large number of cells or molecules identical with a single ancestor.

Cloning Vector: Any plasmid into which a foreign DNA may be inserted to be cloned. It carries foreign DNA into a host bacterial cell upon transformation.

CoA: Coenzyme A.

Cohesive End Sequence (Cos): DNA sequence derived from bacteriophage lambda allowing in vitro packaging.

Cosmid: Plasmid into which bacteriophage lambda cos sites have been inserted; as a result, the plasmid DNA (carrying foreign DNA inserts) can be packaged in vitro in the phage coat.

Dalton: unit of mass commonly used in connection with molecular dimensions corresponding to one hydrogen atom.

DNA Ligation: The formation of a chemical bond linking two fragments of DNA.

Eukaryotic Cells: Cells of higher organisms that contain a membrane-surrounded nucleus.

Gene Cluster: A group of genes physically close on the chromosome.

Genome: Entire chromosome set. The sum total of all of an individual's genes.

Hybridization, Colony Hybridization: Technique used to identify bacterial colonies carrying chimeric vectors whose inserted DNA is similar to some particular sequence.

kb: Abbreviation for 1,000 base pairs of DNA or RNA.

NADH: Reduced nicotinamide adenine dinucleotide.

Linker: Short synthetic duplex oligodeoxynucleotide containing the target site for one or more restriction enzymes. It is added to a vector to create a novel polylinker or multiple cloning site (MCS).

Nucleotide: building block, or monomeric unit, of nucleic acids.

Oligonucleotide: A short chain of nucleotides.

Operon: A complete unit of bacterial gene expression and regulation, including structural genes, regulator genes, and control elements in DNA recognized by regulator gene product(s).

Plasmid: Autonomous, self-replicating, extrachromosomal circular DNA.

Plasmid Copy Number: Number of plasmid molecules maintained in bacteria for every host chromosome.

Primer: Short sequence of DNA or RNA that is paired to one strand of DNA and provides a free 3'-OH end at which a DNA polymerase starts synthesis of a deoxyribonucleotide chain.

Prokaryotic Cells: The small, relatively simple cells comprising most microorganisms.

Promoter: Region of DNA responsible for the initiation of transcription.

Restriction Enzyme: Enzyme that recognizes a specific short sequence of DNA and cleaves it.

Restriction Recognition Sequence: DNA sequence specifically recognized by a particular restriction enzyme. Also known as target site.

Shuttle Vector: Bifunctional cloning vector able to replicate in one or more alternative hosts (e.g., *E. coli* and Streptomyces).

Southern Blotting: The procedure for transferring denatured DNA from an agarose gel to a nitrocellulose filter where it can be hybridized with a complementary nucleic acid probe.

Subcloning: Transferring cloned fragments of DNA from one type of vector to another, for example, from a recombinant cosmid to a plasmid. The new recombinant plasmid is then transformed into an appropriate host cell to produce a subclone strain.

Transcription: Synthesis of RNA from a DNA template.

Transformation of Bacterial Cells: Describes the acquisition of new genetic markers by incorporation of added DNA.

SUMMARY OF THE INVENTION

This invention relates to an isolated DNA segment that encodes for the branched-chain alpha-ketoacid dehydrogenase complex of an organism belonging to the genus Streptomyces.

This invention also relates to an isolated DNA segment, as described above, that further comprises a DNA region that regulates the expression of such branched-chain alpha-ketoacid dehydrogenase complex.

This invention also relates to an isolated DNA segment that encodes for the *Streptomyces avermitilis* branched-chain alpha-ketoacid dehydrogenase complex.

This invention also relates to a DNA segment comprising the DNA sequence of SEQUENCE ID NO. 1, SEQUENCE ID NO. 2, SEQUENCE ID NO. 3, SEQUENCE ID NO. 4 or SEQUENCE ID NO. 5, as described below, or an alleleic variation of such sequence. It also relates to a DNA segment that is a subset of the foregoing DNA segment and functionally equivalent to it.

This invention also relates to: (a) recombinant DNA comprising the DNA sequence of SEQUENCE ID NO. 1, SEQUENCE ID NO. 2, SEQUENCE ID NO. 3, SEQUENCE ID NO. 4 or SEQUENCE ID NO. 5, or an alleleic variation of such sequence; (b) a plasmid comprising such recombinant DNA; and (c) a host cell into which such recombinant DNA has been incorporated.

This invention also relates to the genes for branched-chain alpha-ketoacid dehydrogenase complex contained in a DNA segment selected from the group consisting of pCD528, pCD545, pCD574, pCD550, pCD559 and pCD577, as defined below.

This invention also relates to a method of producing a natural avermectin comprising fermenting, under conditions and in a fermentation medium suitable for producing such natural avermectin, *S. avermitilis* in which the copy number of the genes encoding for the branched-chain alpha-ketoacid dehydrogenase complex has been increased.

This invention also relates to a method of producing a natural avermectin comprising fermenting, under conditions and in a fermentation medium suitable for producing such natural avermectin, *S. avermitilis* in which expression of the genes encoding for the branched-chain alpha-ketoacid dehydrogenase complex has been enhanced by manipulation or replacement of the genes responsible for regulating such expression.

This invention also relates to a method of producing a novel avermectin comprising fermenting, under conditions and in a fermentation medium suitable for producing such novel avermectin, *S. avermitilis* in which expression of the branched-chain alpha-ketoacid dehydrogenase complex has been decreased or eliminated, for example by manipulation (e.g., deletion, inactivation or replacement) of the genes responsible for such expression.

This invention also relates to a DNA Segment comprising the DNA sequence of SEQUENCE ID NO. 1, SEQUENCE ID NO. 2, SEQUENCE ID NO. 3, SEQUENCE ID NO. 4, or SEQUENCE ID NO. 5, or an allelic variation of such sequence.

This invention also relates to a DNA segment comprising a DNA sequence that is a subset of the DNA sequence of SEQUENCE ID NO. 1, SEQUENCE ID NO. 2, SEQUENCE ID NO. 3, SEQUENCE ID NO. 4 or SEQUENCE ID NO. 5, or an alleleic variation thereof, and that is capable of hybridizing to, respectively, SEQUENCE ID NO. 1, SEQUENCE ID NO. 2, SEQUENCE ID NO. 4 or SEQUENCE ID NO. 5, or an alleleic variation thereof, when used as a probe, or of amplifying all or part of such sequence when used as a polymerase chain reaction primer.

This invention also relates to a substantially purified polypeptide comprising the amino acid sequence of SEQUENCE ID NO. 6, SEQUENCE ID NO. 7, SEQUENCE ID NO. 8 or SEQUENCE ID NO. 9.

BRIEF DESCRIPTION OF THE DRAWINGS

FIG. 1: The nucleotide sequence of the polymerase chain reaction (PCR) primers utilized to clone a fragment of the *S. avermitilis* E1-alpha BCKDH gene (SED ID NOS. 10 and 11). The deduced amino acid sequence encoded by each oligodeoxynucleotide are shown above the corresponding DNA sequences. Arrows indicate direction of amplification.

FIG. 2: Branched-chain alpha-keto acid dehydrogenase sequence comparison. Alignment of the deduced amino acid sequences for *Streptomyces avermitilis* (Sa) PCR-cloned CD503 genomic fragment, *Bacillus stearothermophilus* (Bs), *Pseudomonas putida* (Pp), and *Homo sapiens* (Hs). Vertical marks denote amino acid identities. Location of sequences corresponding to rightward and leftward PCR primers used for cloning are indicated (top left and right, respectively).

FIG. 4: Nucleotide sequence and deduced translation products of the 2,728-bp *S. avermitilis* genomic DNA fragment containing the E1-alpha, E1-beta and E2 (partial) bkd open reading frames (ORFs) (SEQ ID NO. 5). E1-alpha ORF extends from positions 403 to 1548 of the sequence, E1-beta ORF extends from positions 1622–2626, and E2 ORF starts at position 2626. Nucleotides are numbered at the top of the sequence lines. Stop codons are indicated by an asterisk (*). Probable Shine-Dalgarno ribosome binding sequences are underlined. BamHI restriction recognition sequences are boxed.

FIG. 5: Nucleotide sequence and deduced translation products of the 0.8-kb BglII-SphI *S. avermitilis* genomic DNA fragment (pCD539) containing part of the E2 bkd ORF(SEQ ID NO. 251 bp were sequenced starting from the BglII site (boxed). Nucleotides are numbered at the top of the sequence lines.

FIG. 6: The nucleotide sequence of the polymerase chain reaction (PCR) mutagenic (rightward) and universal (leftward) primers used to construct pT7 derivatives for heterologous expression of *S. avermitilis* bkd genes in *E. coli* (SEQ ID NOS. 12–15). PCR primers were utilized to introduce an NdeI restriction site at the translational start codon of E1-alpha or E1-beta *S. avermitilis* bkd ORFs (primer pair 55:31 and 56:30, respectively). The deduced amino acid sequence encoded by each mutagenic oligodeoxynucleotide are shown above the corresponding DNA sequences. Restriction recognition sequences are indicated. Arrows indicate direction of amplification.

DETAILED DESCRIPTION OF THE INVENTION

Figure 3:
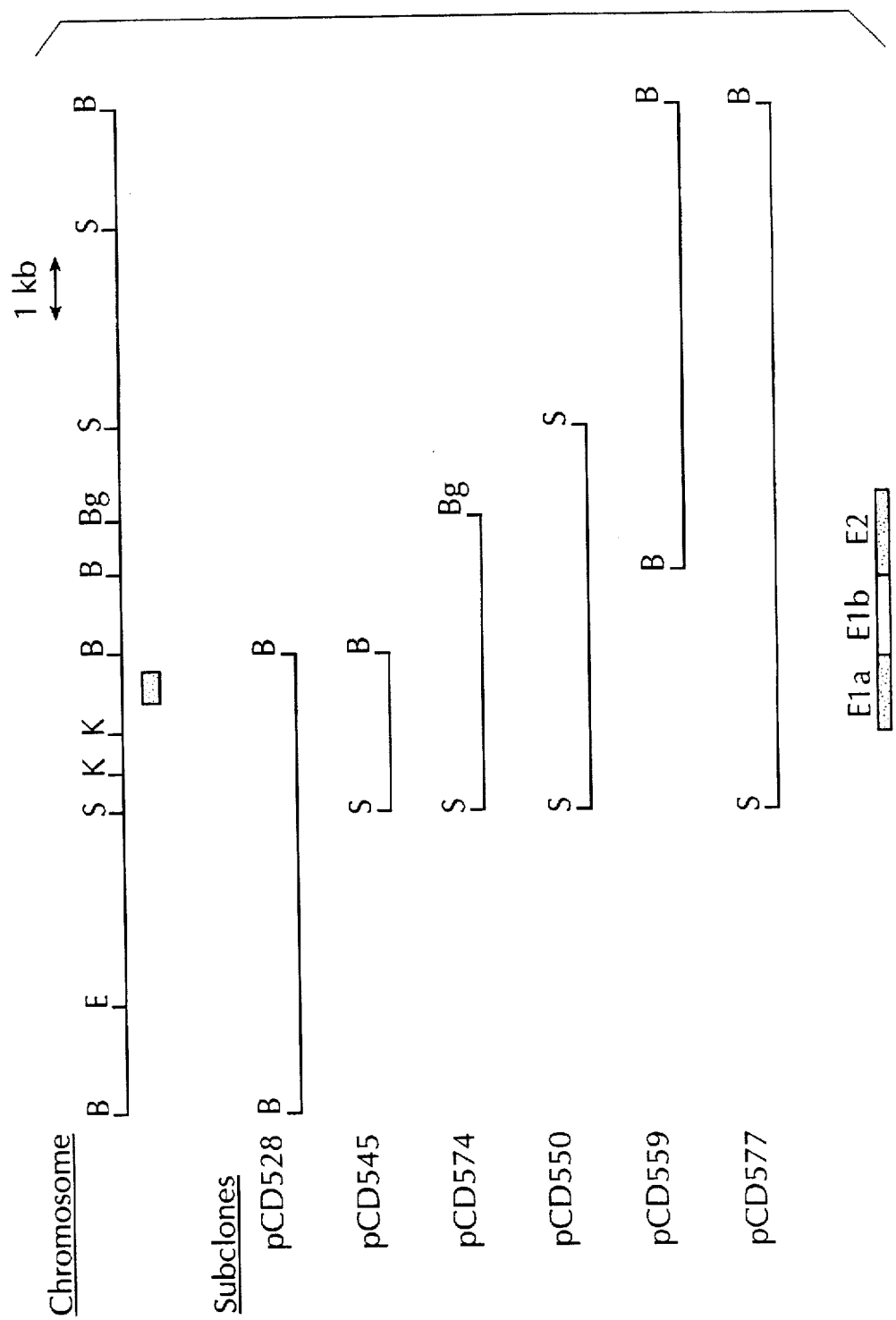
FIG. 3: Genomic restriction map, location and subclones for the *Streptomyces avermitilis* bkd gene cluster. The black box below the map indicates the location and orientation of the initial E1-alpha-specific *S. avermitilis* CD503 genomic fragment cloned using PCR. Genomic subclones (derivatives of pGEM-3Z) are indicated. The location and organization of the bkd structural genes encoding E1-alpha (E1a), E1-beta (E1b), and E2 BCKDH subunits are also indicated. Polarity of identified open reading frames (denoted by boxes) is left to right. Abbreviations: B, BamHI; E, EcoRI; K, KpnI; Bg, BglII; and S, SphI.

The novel procedures for cloning *S. avermitilis* bkd genes and the determination of the primary structure of the genes encoding the *S. avermitilis* BCKDH multienzyme complex are described below.

First, 2 PCR primers, named "Rightward" and "Leftward" (FIG. 1), were designed upon conserved regions identified from a multiple alignment of deduced E1-alpha BCKDH peptide sequences from various species and available from the literature. A PCR product, approximately 0.2 kb long, was detected by amplification of *S. avermitilis* genomic DNA using both the rightward and the leftward primers. That PCR-amplified DNA fragment was subsequently cloned into the *E. coli* vector pGEM-3Z to produce recombinant plasmid pCD503. Subsequently, plasmid pCD503 was transformed into *E. coli* DH5-alpha competent cells. One transformant was designated as strain CD503. DNA sequencing of cloned DNA fragment CD503 showed the existence of an open reading frame with a deduced peptide highly homologous to E1-alpha BCKDH subunit (FIG. 2). Cloned CD503 genomic DNA fragment was then used as a probe to screen a *S. avermitilis*. chromosomal library by colony hybridization. Four cosmid clones were identified, namely CD518, CD519, CD520, and CD521. Restriction and Southern blot analyses showed that the four clones carried overlapping genomic fragments. DNA sequencing of nested deletions from subcloned genomic DNA fragments (as fully described in Example #8) demonstrated that sequence CD503 was part of a complete bkd gene cluster. Cloned *S. avermitilis* bkd genes encompass a region of the chromosome approximately 15 kilobases in length (FIG. 3). DNA sequence analysis showed the presence of putative transcriptional promoter sequences and bkd structural genes arranged as a cluster organized as follows: promoter sequence, E1-alpha, E1-beta, and E2 open reading frames (FIGS. 4 and 5).

Finally, the complete *S. avermitilis* bkd gene cluster, was cloned downstream of the strong *Escherichia coli* T7 promoter for expression in an *E. coli* host. Similarly, the E1-alpha and E1-beta open reading frames (ORFs) were also cloned either separately or together downstream of the T7 promoter and each construction was tested for expression. Novel PCR mutagenic primers, used to introduce unique NdeI restriction site at the ATG translational start of the E1-alpha and E1-beta ORFs, are fully described in the Example #9 (see also FIG. 6). The dual plasmid T7 expression system study demonstrated that at least two open reading frames of the CD503-derived *S. avermitilis* bkd gene cluster (E1-alpha and E1-beta) are fully translatable when expressed in *E. coli*. In addition, enzymatic assays aimed to analyze specifically the E1 component of the BCKDH complex confirmed conclusively that two of the recombinant *E. coli* clones—one carrying the whole bkd gene cluster, and other carrying together the E1-alpha and the E1-beta ORFs, contained E1 BCKDH-specific enzyme activity (Table I).

We describe the isolation of the bkd genes from the avermectin-producer *Streptomyces avermitilis*. The large Streptomyces genome (about 104 kb) is more than twice that of *Escherichia coli*. The streptomycetes genome is composed of DNA of extremely high guanosine plus cytosine (G+C) content (averaging up to 73%, with some regions>90%), close to the upper limit observed in nature. These distinctive characteristics necessitate the development of streptomycetes-specific recombinant DNA techniques. Examples of these efforts can be found in U.S. patent application Ser. No. 08/048,719, filed Apr. 16, 1993 and U.S. patent application Ser. No. 08/032,925, filed Mar. 18, 1993. These applications are incorporated herein by reference in their entirety.

Other techniques specifically optimized for the purpose of this invention, such as PCR genomic DNA amplification, production of nested deletions, DNA sequencing, and heterologous expression of the *S. avermitilis* bkd genes in *E. coli*, are described with full details in the Examples section.

A full description of the experimental steps involved in the cloning of the *S. avermitilis* bkd genes, and results obtained, follows:

(a) Identification of conserved regions in the E1-alpha BCKDH peptide subunit that could serve as candidate sites for binding of PCR primers Four E1-alpha BCKDH peptide sequences from human (Fisher et al., 1989, J. Biol. Chem. 264:3448–3453), rat (Zhang et al., 1987, J. Biol. Chem., 262:15220–15224), *Pseudomonas putida* (Sokatch et al., 1988, Eur. J. Biochem., 176:311–317), and *Bacillus stearothermophilus* (Perham et al., 1990, Eur. J. Biochem., 191:337–346) were aligned to identify conserved regions that could serve as candidate sequences to design corresponding PCR primers. Computer analysis to identify regions of the E1-alpha subunit that are highly conserved in both prokaryotic and eukaryotic BCKDH complexes was done using the LineUp and Pretty programs from the GCG sequence analysis software package (Madison, Wis.). Multiple alignment of the four E1alpha BCKDH peptides showed several regions of extended homology (see Wexler, I. D. et al., 1991, FEBS Letters, 282:209–213). The thiamin pyrophosphate binding motif (Perham et al., 1989, FEBS Letters, 255:77–82) located between human E1-alpha amino acids 182–229, and a region encompassing phosphorylation sites 1 and 2, spanning amino acids 245–289 were notably conserved in all four E1-alpha BCKDH peptides analyzed. Also present was a previously described region of high homology located between amino acids 291–307. This region appears to be unique to alpha-ketoacid dehydrogenases which have both alpha and beta subunits, and is not homologous to any sequence in *E. coli* PDC E1 or the E1 components of *E. coli* and yeast alpha-ketoglutarate dehydrogenase complexes, which are dimers composed of only a single E1 polypeptide. For the above mentioned reasons, the latter region of homology has been suggested to play a role in subunit interaction (Patel et el., 1991, FEBS Letters, 282:209–213). Conserved regions chosen for PCR primer design encoded amino acid residues 192 to 200, and 370 to 376 of the human E1-alpha BCKDH protein.

(b) Design of novel oligonucleotides derived upon those E1-alpha BCKDH conserved regions to be used as PCR primers As previously discussed, two conserved regions of the E1-alpha BCKDH subunit were selected from the multiple alignment study. The Rightward PCR primer (FIG. 1) was designed upon a region encompassing amino acids 192–200 of the human E1-alpha BCKDH subunit -which was used as a representative model of an E1-alpha BCKDH subunit. These amino acids are located within the thiamin pyrophosphate binding motif. The Leftward PCR primer (FIG. 1) was designed upon a region encompassing amino acids 370–376 of the E1-alpha BCKDH subunit. The latter amino acid sequence is located near the C-terminal region of the peptide. Streptomyces gene codon assignments were used (F. Wright and M. J. Bibb, 1992, Gene, 113:55–65). At the 5'-end of each primer there is a restriction enzyme recognition sequence (EcoRI in the rightward primer, and XbaI in the leftward primer) to facilitate the cloning of the PCR products. The complete sequence of the Rightward PCR primer is:

5'-GAATTCGGCGACGGCGCCACCTCCGAGGGC GAC-3' SEQ ID NO. 10.

The complete sequence of the Leftward PCR primer is:

5'-TCTAGACCGCAGGTGGTCCGGCATCTC-3' SEQ ID NO. 11.

Sequences not homologous to the E1-alpha bkd. genes and incorporated into the primers for cloni(c) PCR amplification of S. avermitilis FIG. 1).

(c) PCR amplification of S. avermitilis genomic DNA fragments

S. avermitilis genomic DNA was enzymatically amplified using reaction conditions appropriate for DNA with a high GC content, allowing efficient and specific S. avermitilis genomic DNA was enzymatically amplified using reaction conditions appropriate for DNA with a high GC content, allowing efficient and specific amplification of streptomycetes DNA (see Example 2). PCR was performed using the primer combination described above (Rightward primer SEQ ID NO. 10, 5'-GAATTCGGCGACGGCGCCACCTCCGAGGGCGA C-3', and Leftward primer SEQ ID NO. 11, 5'-TCTAGACCGCAGGTGGTCCGGCATCTC-3'). The amplification products were size fractionated by agarose gel electrophoresis. Under the PCR conditions described above, a single DNA band (approximately 250 base pairs long) was detected when using this primer combination.

(d) Cloning of amplified genomic DNA fragment into Escherichia coli cloning vector, and subsequent transformation into E. coli host As mentioned before, an EcoRI restriction site was incorporated into the Rightward PCR primer for cloning convenience, and a XbaI restriction site was present in the 5' end of the Leftward primer. However, attempts to clone the 0.25 kb PCR fragment by using a ligation procedure where both insert and cloning vector were digested with EcoRI and XbaI were not successful. Therefore, an alternative approach for cloning the 0.25 kb PCR fragment, involving the use of the Klenow fragment of the DNA polymerase I to produce blunt ends in the PCR fragment was explored. A single recombinant clone was recovered after inserting the blunt ended fragment into a blunt-ended, SmaI-linearized E. coli vector (pGEM-3Z[f+]), to produce recombinant plasmid pCD503. Subsequently, pCD503 was introduced into E. coli DH5-alpha competent cells by transformation. The selected transformant was designated as strain CD503. Confirming restriction analysis showed that plasmid pCD503 -isolated from E. coli strain CD503- indeed contained the 0.25 kb S. avermitilis insert.

(e) Subcloning of the 0.25 kb PCR-amplified DNA insert into bacteriophage M13, DNA sequencing of cloned fragment, and identification of bkd-specific sequences.

The 0.25 kb insert present in plasmid pCD503 was subcloned into bacteriophage M13. To accomplish this, first the insert was released from the E. coli vector by digesting pCD503 with EcoRI and PstI, two restriction enzymes whose recognition sequences were present in the multiple cloning site of the pGEM vector at both sides of the cloned insert. The specific fragment was then cloned both into EcoRI-treated, PstI-treated M13 mp18 and mp19 vectors. Cloning into both vectors assures the possibility to produce single-stranded DNA of both strands of the insert DNA for sequencing. One clone, containing the specific insert, selected from the mp18 transfection experiment was named strain CD505. Another clone, also containing the specific insert, but selected from the mp19 transfection experiment, was named CD506. DNA sequencing was performed by the dideoxynucleotide-chain termination method, with a single-stranded DNA template and the TaqTrack kit (Promega). In all cases both strands of DNA-one derived from clone CD505, the complementary strand derived from clone CD506- were sequenced. Codon preference analysis (GCG sequence analysis software package, Madison, Wis.) of the DNA sequencing data obtained from clones CD505 and CD506 showed the existence of an open reading frame having the right codon usage for a streptomycetes gene.

Next, the putative open reading frame was translated into an amino sequence using the Seq and Translate programs of the IntelliGenetics Suite software (IntelliGenetics Inc., Mountain View, Calif.). Finally, data bank similarity searches with the query peptide sequence were run using the FASTDB program of the IntelliGenetics software. All data bank searches, either searching DNA data banks (GertBank and EMBL) or protein data banks (PIR and Swiss-Prot), unequivocally showed that the sequence derived from clone CD503 was highly homologous but novel and distinct to all other E1-alpha BCKDH peptide listed in the data banks, from both prokaryotic and eukaryotic origin. A multiple alignment of E1-alpha BCKDH peptide sequences from human, rat, *Pseudomonas putida* and *Bacillus stearothermophilus*, and including the novel *Streptomyces avermitilis* E1-alpha BCKDH CD503 peptide sequence is shown in FIG. 2. From these data, it can be concluded that the 250 bp S. avermitilis genomic PCR product cloned in E. coli strain CD503 represents indeed a novel E1-alpha bkd gene fragment.

(f) Cloning of the whole S. avermitilis bkd gene cluster, restriction and Southern blot analyses, and construction of chromosomal map An approximately 0.25 kb long BamHI/EcoRI DNA fragment from pCD503, carrying the E1-alpha bkd-specific S. avermitilis DNA sequence was used as a radioactively-labeled probe to screen a S. avermitilis genomic DNA cosmid library by colony hybridization. Four clones (CD518, CD519, CD520, and CD521) were identified and recovered. Restriction and Southern blot hybridization analyses showed that the four clones contain overlapping sequences originated from the same chromosomal region. The same probe was used at high stringency against Southern blots of digested chromosomal DNA from S. avermitilis. ATCC 31272. The latter analysis confirmed the identity of the clones recovered from the genomic library. A restriction map of the genomic region containing the S. avermitilis CD503 sequence is shown in FIG. 3.

(g) Subcloning of genomic DNA fragments derived from clones CD518 and CD521, and DNA sequencing of the S. avermitilis chromosomal region carrying bkd gene cluster Genomic fragments (1–2 kb long) covering the entire CD503 bkd region of the S. avermitilis chromosome were subcloned from DNA library clones CD521 and CD518 into the E. coli vector pGEM-3Z. A list of the subclones constructed during this work, including a brief description of each plasmid, follows: 1. Plasmid pCD528 contains a 7 kb BamHI fragment subcloned from pCD518; 2. Plasmid pCD545 contains a 2.3 kb SphI fragment subcloned from pCD528; 3. Plasmid pCD550 contains a 6 kb SphI fragment subcloned from pCD521; 4. Plasmid pCD559 contains a 7 kb BamHI subcloned from pCD521; 5. Plasmid pCD574 contains a 4.2 kb SphI-BglII fragment subcloned from pCD550; and 6. Plasmid pCD577 contains an approximately 10.4 kb insert. This insert contains 2 adjacent genomic fragments assembled back together: a 4.2 kb SphI/BglII fragment subcloned from pCD550, and a 6.2 kb BglII/BamHI fragment subcloned from pCD559. Plasmid restriction mapping, Southern hybridization, and PCR analysis confirmed the identity of each subclone. The Sanger chain-termination method was used for the determination of nucleotide sequence. To this purpose, S. avermitilis genomic fragments were subsequently subcloned into M13mp18 and M13mp19 bacteriophages to determine the sequence of both DNA strands. Several DNA restriction fragments were isolated from the pGEM-derived clones mentioned above and ligated into M13mp18 and M13 mp19, and the following recombinant phages resulted:

CD535: 0.4 kb *S. avermitilis* DNA fragment cloned by PCR using pCD528 DNA as template, specific primer 29-PCR-EX (5'-AAGAATTCTCGAGCTGGCCCACAAGGCCGTC GGCTAC-3') and universal primer 31-PCR-BP (see Example #9 and FIG. 6). Amplified fragment was restricted with EcoRI and PstI and cloned into EcoRI/PstI linearized M13mp18 DNA.

CD536: Similar DNA fragment as described above cloned into M13mp19 DNA.

CD537: 1.15 kb SalI DNA fragment carrying sequence CD503 subcloned from pCD528 into M13mp18.

CD538: 1.15 kb SalI pCD528 DNA fragment (located upstream of the 1.15 kb SalI fragment described above) cloned into M13mp18.

CD539: 1.5 kb BamHI/BglII DNA fragment subcloned from pCD550 into M13mp18.

CD540: Similar DNA fragment as described above cloned in the opposite orientation in M13mp18.

CD541: 0.35 kb SalI/BamHI DNA fragment subcloned from pCD528 into M13mp18.

CD542: 0.35 kb SalI/BamHI DNA fragment subcloned from pCD528 into M13mp19.

CD553: 0.8 kb BamHI/BglII DNA fragment subcloned from pCD550 into M13mp18.

CD554: 1.1 kb BamHI DNA fragment subcloned from pCD550 into M13mp18.

CD555: Similar DNA fragment as described above cloned in the opposite orientation in M13mp 18.

CD558: 0.8 kb BamHI/HindIII DNA fragment subcloned from pCD553 into M13mp19.

CD561: 1.15 kb SalI DNA fragment subcloned from pCD537 into M13mp18 (opposite orientation to that present in construct CD537).

CD565: 1.15 kb SalI DNA fragment subcloned from pCD537 into M13mp19.

CD566: 1.15 kb SalI DNA fragment subcloned from pCD537 into M13mp19 (opposite orientation to that present in construct CD565).

CD567: 1.15 kb SalI DNA fragment subcloned from pCD538 into M13mp19.

CD582: 0.8 kb BamHI/BglII DNA fragment subcloned from pCD550 into M13mp18 (opposite orientation to that present in CD553).

The *S. avermitilis* genomic inserts carried by these clones were subsequently shortened by treatment with Exonuclease III to provide a series of subclones ("nested deletions", see Example #8).

(h) Computer analysis of DNA sequencing data obtained from cloned DNA fragments and identification of *S. avermitilis* E1-alpha, E1-beta, and E2 bkd open reading frames Nucleotide sequence of the 2.7 kb *S. avermitilis* genomic region containing the bkd genes is shown in FIG. 4. Sliding base composition analysis of the 2.7-kb genomic region containing the *S. avermitilis* E1-alpha, E1-beta and E2 (partial) bkd open reading frames (ORFs) was performed using the "DNA Inspector" software. This analysis provided a profile of the running average of the G+C content using a stretch length of 30 bases and an offset value of 20. Overall G+C content corresponding to this region of the *S. avermitilis* chromosome was 72%. A low G+C valley (G+C content about 50%)—indicative of a promoter region—was located immediately upstream of the bkd Open Reading Frames.

The G+C content as a function of codon position was also analyzed. Open reading frames were detected by using the program "CodonPreference" (Genetics Computer Group, Madison, Wis.) with a Streptomyces codon usage table for 64 genes (F. Wright and M. J. Bibb, 1992, Gene, 113:55–65). The CodonPreference program is a frame-specific gene finder that tries to recognize protein coding sequences by virtue of their similarity to a codon frequency table or by the bias of their composition (usually GC) in the third position of each codon. ORFs were shown as boxes beneath the plot for their respective reading frames. All start (ATG) and stop codons were also detected (vertical lines). Rare codons found in each reading frame were marked below each ORF plot. The G+C content was calculated by using a sliding window of 25 codons, so a lag of about 25 codons was expected before the full impact of a protein-coding region was observed. Three profiles were obtained, as follows: 1, First position in triplet; 2, second position in triplet; 3, third position in triplet. As a result of this analysis, three bkd ORFs were located, corresponding to the following BCKDH subunits: E1-alpha, E1-beta, E2 (FIGS. 4 and 5).

(i) Design of novel oligonucleotides to be used as primers for PCR-based, site-directed mutagenesis Linker or PCR-based, site-directed mutagenesis was used to introduce a NdeI restriction site at the ATG translational start site of the E1-alpha and E1-beta ORFs. The following novel oligonucleotides were designed (see also Example #9 and FIG. 6):

Leftward Universal (Vector) Primers:
30-PCR-BP:
5'-AAGGATCCTGCAGCCCAGTCACGACGTT GTAAAACGA-3', SEQ ID NO. 12
31-PCR-BP:
5'-AAGGATCCTGCAGACAGCTATGACCATG ATTACGCCA-3', SEQ ID NO. 13

Rightward Mutagenic Primers:
55-PCR:
5'-AAGAGATCTCATATGACGGTCATGGAGC AGCGG-3', SEQ ID NO. 14
56-PCR:
5'-AAGAGATCTCATATGACCACCGTTGCCCT GAAG-3', SEQ ID NO. 15

(j) Site-directed mutagenesis of *S. avermitilis* bkd genes to create novel NdeI restriction site upstream of an open reading frame Expression plasmids were derivatives of plasmid pT7-14 7 (see S. Tabor, 1990, In Current Protocols in Molecular Biology, pp. 16.2.1–16.2.11. Greene Publishing and Wiley-Interscience, New York) carrying E1-alpha, E1-beta, E1-alpha plus E1-beta ORF's, or the complete *S. avermitilis* bkd gene cluster. NdeI restriction sites were created by PCR-based, site-directed mutagenesis. Five expression plasmids were constructed for this study as follows:

Plasmid pCD670: Derivative of pT7-7 carrying the *S. avermitilis* E1-alpha bkd open reading frame (ORF1). An NdeI restriction site spanning the ATG start codon was introduced into the *S. avermitilis* E1-alpha bkd gene by amplification and concomitant mutagenesis using the PCR mutagenic primer 55-PCR (see Example #9 and FIG. 6).

Plasmid pCD666: Derivative of pT7-7 carrying the *S. avermitilis* E1-beta bkd open reading frame (ORF2).

An NdeI restriction site spanning the ATG start codon was introduced into the *S. avermitilis* E1-beta bkd gene by amplification and concomitant mutagenesis using the PCR mutagenic primer 56-PCR (see Example #9 and FIG. 6). To attain optimal expression of this ORF, the third position of codon 7 was changed from C to G to produce a codon synonym resembling the *E. coli* codon usage. The E1-beta peptide sequence was not affected by this change.

Plasmid pCD736: Derivative of pT7-7 carrying together both E1-alpha (ORF1) and E1-beta (ORF2) ORFs under the control of the T7 promoter.

Plasmid pCD705: Similar to pCD736 but having the 3'-half of the E1-beta ORF located in the wrong orientation. This construct was used as a negative control in expression experiments.

Plasmid pCD685: Derivative of pT7-7 carrying the complete *S. avermitilis* bkd gene cluster.

(k) Expression of *S. avermitilis* bkd open reading frames in *E. coli* by using the T7 dual plasmid expression system Expression of the *S. avermitilis* bkd genes in *E. coli* was achieved using the T7 RNA polymerase/promoter dual plasmid system essentially as described by S. Tabor (1990. In Current Protocols in Molecular Biology, pp. 16.2.1–16.2.11. Greene Publishing and Wiley-Interscience, New York). Derivatives of *E. coli* C600 (pGP-1) containing the different pT7-7 constructions were analyzed. Sodium dodecyl sulphate—polyacrylamide gel electrophoresis (SDS-PAGE) was used to monitor the expression of the *S. avermitilis* ORFs in the *E. coli* host after heat induction. SDS-PAGE analysis of protein profile upon induction showed overexpression of induced peptides having a size similar to the predicted value (as deduced from the corresponding DNA sequence) for the E1-alpha and the E1-beta ORFs, as follows:

|  | Predicted Size (Da) | Observed Size (Da) |
| --- | --- | --- |
| ORF1 (E1-alpha) | 41,000 | 41,000 |
| ORF2 (E1-beta) | 35,000 | 34,000 |

(l) Detection of E1 *S. avermitilis* BCKDH activity by specific assay in crude extract of recombinant *E. coli* clone Table I below (Example 11) summarizes these results. E1-specific BCKDH assays performed in crude extracts of *E. coli* cells carrying pCD736 showed significant E1 activity upon induction of the T7 promoter. A similar culture carrying a construct with part of the insert positioned in the wrong orientation (pCD705), showed background level of activity.

In addition, enzymatic assays indicated that crude extracts from the *E. coli* strain containing plasmid pCD685 also have a significant E1 BCKDH activity (>10-fold background level). An uninduced culture of this clone was also analyzed and showed a basal level of activity 2-fold above background. The latter result is expected since the T7 system is known to allow a low level of constitutive expression of the cloned genes even under uninduced conditions.

The cloned *Streptomyces avermitilis* bkd gene cluster is useful in improving natural avermectin production by increasing the copy number of these genes or by optimizing their expression in production strains. One possible approach to achieve efficient expression of the cloned bkd genes involves the insertion of these genes into a multicopy *E. coli* /streptomycetes shuttle vector (e.g., plasmid pCD262, Denoya C. D., 1993, "Novel Bacterial Plasmids Shuttle Vectors for Streptomycetes and *Escherichia coli*", U.S. patent application Ser. No. 08/032,925, filed Mar. 18, 1993) such that the genes are transcribed from a strong promoter. This procedure will ensure efficient transcription of the genes. In addition, certain strategies can be devised to guarantee efficient expression. These include (a) promoter strength; (b) the stability of the mRNA; (c) presence or absence of regulatory factors; (d) inducibility; and (e) site directed mutagenesis to improve ribosome recognition and translation initiation signals. Expression of the bkd genes could also be optimized by replacing the wild type promoter and regulatory regions with different promoters by gene replacement techniques. There are many examples in the literature of useful promoters that could be employed to optimize the expression of the novel *S. avermitilis* bkd genes disclosed here, e.g., the strong ermE promoter (Hopwood et al., 1985, "Genetic Manipulation of Streptomyces: A Laboratory Manual", The John Innes Foundation, Norwich, U.K.) and the thiostrepton-inducible tipA promoter (Murakami et al., 1989, J. Bacteriol, 171, 1459– 1466). Additionally, inactivation of the bkd genes, and concomitant absence of BCKDH activity, by deletion or site-directed mutagenesis using gene replacement techniques will develop improved, irreversibly blocked bkd *Streptomyces avermitilis* strains which are useful in the production of novel avermectins.

EXAMPLES

The following are detailed Examples of the experimental procedures used to clone and analyze the bkd genes from *S. avermitilis*, which are also illustrated in the accompanying Figures. Additional details of standard techniques, which are well known to those skilled in molecular biology, and the designation of the particular enzymes used, are described, for example, in the laboratory manual "Molecular Cloning by Maniatis et al (Cold Spring Harbor Laboratory, 1989).

Example 1

Preparation of *S. avermitilis* Genomic DNA

*S. avermitilis* ATCC 81272 mycelium was grown as a confluent lawn on YPD-2 agar medium for 7 days at 29° C. The medium comprised:

| | |
| --- | --- |
| Difco Yeast Extract | 10 grams |
| Difco Bacto-peptone | 10 grams |
| Dextrose | 5 grams |
| Difco Bacto agar | 20 grams |
| Sodium acetate | 2 grams |
| MOPS | 10 grams |
| pH adjusted to 7.0. | |
| Final volume: 1 L. | |
| Autoclaved for 25 minutes at 121° C. | |

The grown mycelium was then used to inoculate 30 ml of AS-7 medium (see Hafner et al., 1988, European Patent Application # 88300353.5, publication #0 284176) in a 300-ml baffled flask, which was maintained with shaking (230 rpm) at 29° C. for 24 hours. The medium comprised:

| | |
| --- | --- |
| Thinned starch[1] | 20 grams |
| Ardamine pH[2] | 5 grams |
| Pharmamedia[3] | 15 grams |
| Calcium carbonate ($CaCO_3$) | 2 grams |
| pH adjusted to 7.2 with sodium hydroxide (NaOH). | |
| Final volume: 1 L. | |
| Autoclaved for 25 minutes at 121° C. | |

-continued

[1] Prepared by hydrolysis of starch by alpha-amylase from *Bacillus licheniformis* to a dextrose equivalent of approximately 40%.
[2] From Yeast Products, Inc., Clifton, NJ 07012.
[3] From Traders Protein, Memphis, TN 38108.

Approximately 0.3 ml of the above culture was used to inoculate another 300-ml baffled flask containing 30 ml of modified liquid Yeast Extract Malt Extract (YEME) medium (Bibb, M. J., Freeman, R. F., and D. A. Hopwood, 1977, Mol. Gen. Genetics, 154:155–166). Modified YEME medium contained per liter:

| Difco Yeast extract | 3 grams |
| Difco Bacto-peptone | 5 grams |
| Oxoid Malt extract | 3 grams |
| Sucrose | 300 grams |
| Glucose | 10 grams |
| Autoclaved for 40 minutes at 121° C. | |

2 ml of 2.5M magnesium chloride hexahydrate ($MgCl_2 \cdot 6H_2O$) were added after autoclaving.

Final volume adjusted to 1 L.

Cultures were grown for 48–72 hours at 29° C. Mycelium was recovered by centrifugation and genomic DNA was prepared following the protocol "Isolation of Streptomyces Total DNA by Cesium Chloride Gradient Centrifugation: Procedure 2", as found in the textbook "Genetic Manipulation of Streptomyces, A Laboratory Manual", The John Innes Foundation, Norwich, U.K., 1985, authored by Dr. D. A. Hopwood et al. DNA pellets were resuspended in 3 ml TE buffer (10 mM Tris-HCl, pH 8.0, 1 mM EDTA).

Example 2

Polymerase Chain Reaction *S. avermitilis* Genomic DNA Amplification

*S. avermitilis* genomic DNA was enzymatically amplified by using a Perkin-Elmer Cetus thermal cycler. The PCR reaction was carried out with Taq polymerase (Perkin-Elmer Cetus) and the buffer provided by the manufacturer in the presence of 200 µM dNTP, 15% glycerol, 0.5 µM of each primer, 50 ng of template DNA (in this case, *S. avermitilis* genomic DNA), and 2.5 units of enzyme in a final volume of 100 µl for 30 cycles. The thermal profile of the first cycle was: 95° C. for 3 min (denaturation step), 55° C. for 2 min (annealing step), and 72° C. for 2 min (extension step). Subsequent 29 cycles had a similar thermal profile except that the denaturation step was shortened to 1.5 min. DNA primers were supplied by Genosys Biotechnologies, Inc. (Texas). The Rightward primer (FIG. 1) was 5'-GAATTCGGCGACGGCGCCACCTCCGAGGGCGAC-3' SEQ ID NO. 10, and the Leftward primer (FIG. 1) was 5'-TCTAGACCGCAGGTGGTCCGGCATCTC-3' SEQ ID NO. 11. The amplification products were size fractionated by agarose gel electrophoresis. The PCR sample was electrophoresed in a horizontal 1.5% agarose gel in 1×TBE buffer (90 mM Tris-HCl, pH 8.5, 90 mM boric acid, 2.5 mM ethylenediaminetetraacetic acid (EDTA) for 1.5 hours at 100 V as described by Maniatis et al. The separated PCR DNA products were located in the gel by staining with ethidium bromide and visualizing fluorescent bands with a 365 nm ultraviolet light. Under the PCR conditions described above, a single DNA band (approximately 250 base pairs long) was detected when using this primer combination.

Example 3

Cloning of a 0.25 kb PCR Amplified *S. avermitilis* Genomic DNA Fragment into *E. coli* vector, and Subsequent transformation into *E. coli* host.

A. Recovery of the 0.25 kb PCR Product

As mentioned before, a 0.25 kb DNA fragment was amplified by PCR using *S. avermitilis* genomic DNA as template and the Rightward plus Leftward primer combination. As shown in FIG. 1 the Rightward primer has an EcoRI recognition site located at the 5' end and the Leftward primer has a XbaI recognition site at the 5' end. However, attempts to clone the 0.25 kb PCR fragment by using a ligation procedure where both insert and cloning vector were digested with EcoRI and XbaI were not successful. Therefore, an alternative approach for cloning the 0.25 kb PCR fragment, involving the use of the Klenow fragment of the DNA polymerase I to produce blunt ends in the PCR fragment was explored. Following amplification (as described in Example 2), approximately 80 µl of the PCR reaction were twice extracted with phenol-chloroform, twice extracted with ether, and then, the PCR DNA product was ethanol precipitated as previously described. DNA was resuspended in 18.5 µl $H_2O$. Then, 2.5 µl 10×Nick-translation buffer (0.5M Tris-HCl, pH 7.2, 0.1M magnesium sulfate ($MgSO_4$), 1 mM dithiothreitol, 500 µg/ml bovine serum albumin) (Maniatis et al., 1989) end 20 units of the Klenow fragment of *E. coli* DNA polymerase I (Boehringer Mannheim Biochemicals) were added and the mixture incubated at 37° C. for 5 minutes. Then, 1 µl of 2 mM dNTP (2 mM each of the 4 dNTPs) was added and the reaction incubated further at room temperature for 15 minutes. The repairing reaction was stopped by adding 1 µl of 0.5M EDTA, pH 8.0, and the total content of the reaction mixture was loaded on a 1.5% agarose gel end electrophoresed. The 0.25 kb DNA fragment was visualized as described before and recovered by electroelution as follows: The 0.25 kb DNA band was removed with a razor blade and the DNA recovered from the agarose gel by electroelution for 35 min. at 80 V into a V-shaped well filled with 10M ammonium acetate using an unidirectional electroelutor (International Biotechnology Inc., New Haven, Conn.). The DNA was then precipitated with ethanol, pelleted and finally redissolved in 20 µl of DNA buffer (10 mM Tris-HCl, 4 mM sodium chloride (NaCl), 0.1 mM EDTA; pH 7.5).

B. SmaI Digestion and Dephosphorylation of Plasmid Vector pGEM-3Z

Approximately 1 µg of the plasmid pGEM-3Zf(+) (Promega Corp., Madison, Wis.) and 2 units of the restriction enzyme SmaI (all restriction enzymes were purchased from Boehringer Mannheim Biochemicals) were incubated in the assay buffer specified by the supplier, at 25° C. for 3.5 hours, in a total reaction volume of 40 microliters (µl) to produce linear blunt-ended molecules. Then, the SmaI-linearized vector was dephosphorylated using calf intestine alkaline phosphatase (CIAP) (purchased from Promega Corp., Madison, Wis.) following the instructions obtained from the supplier. The reaction mixture was incubated for 35 min. at 37° C., and the DNA was then extracted twice with an equal volume of phenol-chloroform, twice with an equal volume of ether, and finally the DNA was precipitated by adding 2 volumes of absolute ethanol. Precipitated DNA was recovered by centrifugation at 10,000×G for 10 min. and dried under vacuum. Final pellet was redissolved in 20 µl of DNA buffer.

C. Ligation to Produce pCD503

About 9 µl of the Klenow-treated 0.25 kb PCR DNA product, and about 1 µl of the SmaI-linearized, CIAP-dephosphorylated, blunt-ended pGEM-3Zf(+) were incubated overnight with 1 unit of ligase (New England BioLabs, IC, Beverly, Mass.) under the conditions specified by the supplier at 14° C. in a total reaction volume of 20 µl. The reaction was terminated by placing the assay microtube on ice and 15 µl of the reaction mixture was then used to transform competent *E. coli* JM109 cells following standard procedure as described by Maniatis et el., 1989. Many ampicillin-resistant transformants were recovered. Plasmid vector pGEM-3Zf(+) contains a DNA segment derived from the lac operon of *Escherichia coli* that codes for the amino-terminal fragment of beta-galactosidase (Yanisch-Perron, C., Vieira, J., and J. Messing, 1985, Gene, 33, 103). This fragment, whose synthesis can be induced by isopropylthio-beta-D-galactoside (IPTG), is capable of intra-allelic (alpha) complementation with a defective form of beta-galactosidase encoded by the host. *E. coli* cells exposed to the inducer IPTG synthesize both fragments of the enzyme and form blue colonies when plated on media containing the chromogenic substrate 5-bromo-4-chloro-3-indolyl-beta-D-galactoside (X-gel). Insertion of foreign DNA into the polycloning site of the plasmid inactivates the amino-terminal fragment of the beta-galactosidase and abolishes alpha-complementation. Therefore, bacteria carrying recombinant plasmids give rise to white colonies. Numerous white colonies were recovered from this transformation experiment. These colonies should contain the plasmid pCD503. This was confirmed by selecting one colony, designated as strain CD503, and further analyzing. A single bacterial colony of *E. coli* strain CD503 was inoculated into Luria-Bertani (LB) liquid medium containing 50 µg/ml of ampicillin following standard microbiological procedures. The LB medium comprised:

| | |
|---|---|
| Bacto-tryptone | 10 grams |
| Bacto-yeast extract | 5 grams |
| NaCl | 10 grams |
| pH adjusted to 7.0 with 5N sodium hydroxide (NaOH). | |
| Final volume of the solution adjusted to 1 L. | |
| Sterilized by autoclaving for 20 min at 121° C. | |

The culture was incubated at 35° C. overnight. The following morning, the bacterial cells were harvested by centrifugation at 10,000 rpm for 5 min. at 4° C. Plasmid vector was isolated from freshly harvested *Escherichia coli* CD503 cells using a modification of the method of Birnboim and Doly (Nucleic Acids Res., 1979, 7:1513), as described by Denoya et al, 1985, Microbios Lett., 29:87. The isolated plasmid DNA was finally dissolved in DNA buffer (10 mM Tris-HCl, 4 mM NaCl, 0.1 mM EDTA; pH 7.5) to produce a concentration of approximately 1 µg of pCD503 per 10 µl of buffer. Confirming restriction analysis, using restriction enzymes EcoRI and PstI, showed that, as expected, pCD503 carried the 0.25 kb DNA insert.

Example 4

Preparation of Radiolabeled DNA and RNA Probes

A. Preparation of Uniformly Labeled Double-stranded DNA Probes

Double-stranded DNA probes were prepared by nick translation (see Maniatis et al., 1989, for a general description of this technique). First, a specific DNA fragment carrying the target sequence was prepared by appropriate restriction digestion and purification by electroelution essentially as described in Example 1. Approximately 1 µg of DNA was labeled in each case using [alpha-$^{32}$P]dCTP (deoxycytidine 5'-triphosphate, tetra(triethylammonium) salt, [alpha-$^{32}$P]–) purchased from NEN-Dupont, and the BRL Nick Translation System purchased from BRL Life Technologies, Inc., following the instructions obtained from the supplier. A typical reaction was performed in a volume of 50 µl. After addition of 5 µl of Stop buffer (as described in the BRL recommended procedure), the labeled DNA was separated from unincorporated nucleotides using the Stratagene push column following the instruction manual obtained from the supplier. $^{32}$P-labeled DNA with a specific activity well in excess of $10^8$ cpm/µg was routinely obtained following these procedures.

B. Preparation of Labeled Single-stranded RNA Probes $^{32}$P-labeled RNA probes were prepared by in vitro transcription using the Riboprobe Gemini transcription system (Promega). A purified fragment of the target DNA was cloned into the transcriptional vector pGEM-3Z using standard procedures. Preparation of template plasmid DNA for in vitro transcription reactions was performed as described in Example 3, but including a polyethylene glycol (PEG) precipitation step to selectively remove small nucleotides which may contaminate these preparations, as follows: After the ethanol precipitation step, the pellet was resuspended in 520 µl of water. Then 100 82 1 of 5M NaCl and 620 µl of 13% PEG (MW 6,000–8,000) was added. After mixing, the tube was incubated on ice for 1 hour and the DNA was pelleted at 4° C. at 10,000×G for 15 min. Pellet was washed once with 500 µl of 80% cold ethanol and resuspended as usual. Approximately 1 µg of template plasmid DNA was linearized using either ScaI or HindIII restriction enzymes, and subsequently in vitro transcribed using SP6 or T7 bacteriophage DNA-dependent RNA polymerase, respectively. Cytidine 5'-triphosphate tetra(triethylammonium) salt, [alpha-$^{32}$P] (CTP) purchased from NEN-Dupont was used in this reaction. Reaction conditions were followed as recommended by the supplier. After the incubation, the reaction mixture was treated with 1 unit of RQ1-DNase (Promega) to degrade the DNA template, extracted twice with phenol-chloroform, and then ethanol precipitated following standard procedures. The pellet was dried and resuspended in 20 µl of RNase-free water (Promega). A small aliquot of the labeled RNA transcript was analyzed by polyacrylamide-agarose gel electrophoresis as described by Denoya et al., 1987, J. Bacteriol., 169:3857–3860. Under the conditions described here, labeled full lengths transcripts were obtained routinely.

Example 5

Analysis of *S. avermitilis* Genomic DNA by Southern Hybridization

Approximately 10 µg of purified *S. avermitilis* genomic DNA were digested with 2 units of the restriction enzyme BamHI at 37° C. for a minimum of 2 hours. At the end of the digestion, the DNA fragments were separated by electrophoresis through a 1% agarose gel (see Example 1A), and were transferred overnight to a nylon membrane (pore size 0.45 µm) (Schleicher and Schuell Nytran membranes) using the capillary transfer method (Southern, E. M., 1975, J. Mol. Biol., 98:503). The next day, the nylon membranes were wrapped in plastic wrap and the DNA side of each membrane was exposed to a source of ultraviolet irradiation (302 nm) to fix the DNA to the membrane. Hybridization of radiolabeled RNA or DNA probes to DNA immobilized on nylon membranes was performed following the protocol described in Manitatis et al. (1989). Prehybridization and hybridization were carried out at 42° C. Hybridization solution contained: 6×SSC (1×: 0.15M sodium chloride (NaCl), 15 mM sodium citrate, pH 7.0), 10×Denhardt's reagent [1×: 0.02% ficoll, 0.02% polyvinylpyrrolidone, 0.02% bovine serum albumin], 1% SDS (sodium dodecyl sulfate), 100 µg/ml denatured, fragmented salmon sperm DNA, 100 µg/ml *E. coli* tRNA, and 50% formamide (Fluka). After overnight hybridization, membranes were washed as follows: two washes with 1×SSC, 0.1% SDS, at room temperature for 15 minutes, and two washes with 0.1×SSC, 0.1% SDS at 42° C. for 15 minutes. In some experiments

21 hybridization was carried out at 65° C. in the absence of formamide, and SSPE (1×: 0.18M NaCl, 10 mM sodium phosphate (NaPO$_4$), pH 7.7, 1 mM EDTA) was used instead of SSC. Finally, membranes were exposed to X-ray film to obtain an autoradiographic image.

Example 6

Cloning of the 0.25 kb CD503 *S. avermitilis* genomic fragment into bacteriophage M13 and DNA Sequencing The 0.25 kb CD503 *S. avermitilis* DNA fragment was cloned into bactedophages M13mp18 and M13mp19 for the preparation of single-stranded recombinant DNA to be used as templates in the Sanger's dideoxy sequencing method (Sanger et al., 1977, Proc. Nat. Acad. Sci. USA, 74:5463–5467). About 2 µg of plasmid pCD503, prepared following a miniprep procedure as described before, were digested with the restriction enzymes EcoRI and PstI to release the 0.25 kb *S. avermitilis* genomic insert. Previously, restriction analysis showed that pCD503 digested with EcoRI or with PstI alone was linear. This analysis demonstrated that the 0.25 kb insert did not contain either EcoRI or PstI recognition sites. The digestion mixture was electrophoresed in a 1.2% agarose gel, and the 0.25 kb fragment was electroeluted and precipitated as described before. In addition, about 1 µg each of purified double-stranded replicative form (RF) M13mp18 and M13mp19 DNAs were double digested with EcoRI and PstI, dephosphorylated with calf intestine alkaline phosphatase (CIAP) (purchased from Promega Corp., Madison, Wis.), and finally ligated to the 0.25 kb DNA fragment as described previously. Purified RF M13 cloning vectors were purchased from New England Biolabs. Ligation mixtures were used to transfect competent *E. coli* JM109 cells. A single white plaque from the mp18 transfection, and a single one from the mp19 transfection were selected, phage grown and single-stranded DNA prepared as described (Maniatis et al., 1989). DNA sequencing of each single-stranded DNA template was performed using the M13-specific-40 sequencing primer (New England Biolabs, catalog #π1212), deoxyadenosine 5'-[alpha-thio]triphosphate, [$^{35}$S] (NEN-Dupont), and the TaqTrack sequencing kit (Promega), following the instructions provided by the supplier (Promega). DNA sequencing data of the pCD503 *S. avermitilis* genomic fragment is shown in FIG. 4.

Example 7

Cloning of the whole bkd *S. avermitilis* gene cluster and construction of chromosomal map About 5 µg of purified pCD503 were double restricted using both BamHI and EcoRI restriction enzymes, DNA fragments were separated by electrophoresis in a 1.2% agarose gel, an approximately 0.25 kb long DNA fragment carrying sequence specific for the *S. avermitilis* bkd El-alpha gene was recovered by electroelution, and was labeled by nick translation essentially as described previously. The [$^{32}$P]-labeled DNA fragment was then used as a probe to screen a *S. avermitilis* genomic cosmid library. A detailed description of preparation of genomic libraries in general can be found in Molecular Cloning A Laboratory Manual by Maniatis et al. (1989). A complete description of streptomycetes chromosomal library preparation is presented in Genetic Manipulation of Streptomyces—A Laboratory Manual by Hopwood et al. (1985). A description of cosmid vector is found in "Cosmid Vectors for Streptomyces Genomic DNA Cloning" by Denoya C. D., U.S. patent application Ser. No. 08/048,719, filed Apr. 16, 1993. Four clones were identified after screening more than 2200 recombinant library clones. The four hybridizing clones (recorded as *E. coli* clones CD518, CD519, CD520, and CD521) were grown in LB medium under ampicillin selective pressure. Plasmid was prepared from each culture as described before. Restriction and Southern blot hybridization analyses revealed that the four clones were related, having overlapping chromosomal regions. A *S. avermitilis* genomic restriction map, covering the entire chromosomal region including sequence CD503, was obtained following standard procedures, and is presented in FIG. 3.

Example 8

Generation of Nested Sets of Deletion Mutants for Directed DNA Sequencing of *S. avermitilis* Chromosomal Region Carrying bkd Gene Cluster Nested sets of deletion routants that lack progressively more nucleotides from one end or the other of the *S. avermitilis* bkd target DNAs were generated using Exonuclease III following procedures essentially similar to those described by Henikoff, S. (1987, Methods Enzymol., 155:156). To create unidirectional deletion mutants, the double-stranded DNA of each recombinant bacteriophage M13 replicative form DNA was digested with two restriction enzymes, both of which have sites of cleavage between one end of the target DNA and the primer-binding site. The restriction enzyme that cleaved nearer the target sequences generated a blunt end or a recessed 3' terminus; the other enzyme generated a protruding 3' terminus. Exonuclease III catalyzes the stepwise removal of 5' mononucleotides from a recessed or blunt 3'-hydroxyl termini of double-stranded DNA. However, protruding 3' termini are completely resistant to the activity of the enzyme. Therefore, only one end of the resulting linear DNA was susceptible to exonuclease III, and the digestion proceeded unidirectional away from the site of cleavage into the target DNA sequences.

As an example, the description of the preparation of pCD565 nested deletions follows. Plasmid pCD565 is a M13 mp19 RF derivative carrying a 1.15 kb SalI fragment that contains part of the El-alpha *S. avermitilis* bkd open reading frame. Plasmid pCD565 was purified by equilibrium centrifugation in cesium chloride and ethidium bromide gradients as described by Maniatis et al. (1989). Exonuclease III is able to initiate digestion from single-stranded nicks, so it is important to use a preparation containing less than 10% relaxed circular molecules. About 10/µg of plasmid pCD565 (see section "Detailed description of the Invention") were double digested with restriction enzymes ScaI and XbaI at 37° C. for 4 hours, then phenol-chloroform and ether extracted, and ethanol precipitated as described previously. The pellet was resuspended in 60 µl of Exonuclease III reaction buffer (10×exonuclease III buffer: 0.66M Tris-HCl, pH 8.0, 66 mM magnesium chloride (MgCl$_2$). The DNA solution was then incubated at 37° C. in the presence of 300 units of exonuclease III (Ambion Inc.), and 2.5 µl aliquots were removed at 30-second intervals. Samples were then incubated with nuclease S1 and aliquots of each of the samples were analyzed by agarose gel electrophoresis. Samples containing DNA fragments of the desired size were pooled, DNA was repaired by using the Klenow fragment of the DNA polymerase I, ligated overnight, and transfected into competent *E. coli* JM109 cells. Insert size in recovered clones were analyzed by EcoRI/HindIII restriction and agarose gel electrophoresis. Five clones were selected for sequencing: 565-D19 (1.1 kb), 565-D7 (0.88 kb), 565-d24 (0.77 kb), 565-D1 (0.51 kb), and 565-D16 (0.36 kb). Single stranded DNA was prepared from each of these clones and sequenced as described before.

Example 9

Construction of Plasmids pCD670, pCD666, pCD736, and pCD685 to be used in the Expression of the *S. avermitilis* bkd genes in *E. coli*

Expression of the *S. avermitilis* bkd genes in *E. coli* was achieved using the T7 RNA polymerase/promoter dual plasmid system essentially as described by S. Tabor (1990. In Current Protocols in Molecular Biology, pp. 16.2.1–16.2.11. Greene Publishing and Wiley-Interscience, New York).

A. Construction of pCD670 carrying the *S. avermitilis* E1-alpha bkd ORF:

An NdeI restriction site spanning the ATG start codon was introduced into the *S. avermitilis* bkd E1-alpha gene using a PCR-based procedure. The template for PCR was plasmid pCD528, a pGEM-3Z derivative carrying a 7 kb *S. avermitilis* genomic insert containing the amino terminal half of the E1-alpha ORF. Two oligonucleotides were used as primers in the PCR reaction (see FIG. 6):

1. Leftward Universal (Vector) primer 31 -PCR-BP (5'-AAGGATCCTGCAGACAGCTATGACCATGATTACGCCA-3' SEQ ID NO. 13) which maps downstream the HindIII site of the pGEM-3Z MCS (position 91–114). At the 5'-end of this primer there are two As, and two restriction sites (BamHI and PstI) to facilitate the cloning of the PCR products.

2. Mutagenic primer 55-PCR (5'-AAGAGATCTCATATGACGGTCATGGAGCAGCGG-3' SEQ ID NO. 14.). At the 5' end of this primer there are two As, one G, and two restriction sites (BglII and NdeI). The NdeI site overlaps the ATG initiator codon of the E1-alpha open reading frame.

Polymerase chain reaction was carried out as described before. Reaction products were analyzed by electrophoresis in a 0.8% agarose gel. A PCR-amplified DNA fragment of the correct size (about 1.1 kb long) was electroeluted, digested with restriction enzymes NdeI and BamHI, and subcloned into NdeI/BamHI linearized plasmid pT7-7 to give plasmid pCD663 upon ligation and transformation into *E. coli* DH5-alpha cells. About 1 µg of plasmid pCD663 (prepared from *E. coli* strain CD663 using a plasmid miniprep procedure) was linearized with BamHI, dephosphorylated, and finally ligated in the presence of about 0.5 µg of electroeluted purified 1.1 kb BamHI fragment isolated from a BamHI digestion of plasmid pCD550, to give plasmid pCD670. The correct orientation of the 1.1 kb BamHI fragment in the latter construct was determined by mapping SalI sites present in the insert. Finally, plasmid pCD670 was introduced into *E. coli* strain C600 carrying plasmid pGP1-2 (the plasmid containing the T7 RNA polymerase gene) (see Tabor, 1990). One transformant was selected for further work and recorded as strain CD676.

B. Construction of pCD666 carrying the *S. avermitilis* E1-beta bkd ORF:

An NdeI restriction site spanning the ATG start codon was introduced into the *S. avermitilis* bkd E1-beta gene using a PCR-based procedure. The template for PCR was plasmid pCD574, a pGEM-3Z derivative carrying a 4.5 kb *S. avermitilis* genomic insert containing the E1-beta ORF. Two oligonucleotides were used as primers in the PCR reaction (see also FIG. 6):

1. Leftward Universal (Vector) primer 30-PCR-BP: (5'-AAGGATCCTGCAGCCCAGTCACGACGTTGTAAAACGA-3' SEQ ID NO. 12) maps upstream the EcoRI site of the pGEM-3Z MCS (position 2689–2712). At the 5'-end of this primer there are two As, and two restriction sites (BamHI and PstI) to facilitate the cloning of the PCR products.

2. Rightward Mutagenic primer 56-PCR: (5'-AAGAGATCTCATATGACCACCGTTGCCCTGAAG-3' SEQ ID NO. 15). At the 5' end of this primer there are two As, one G, and two restriction sites (BglII and NdeI). The NdeI site overlaps the ATG initiator codon of the E1-beta open reading frame. Polymerase chain reaction was carried out as described before. Reaction products were analyzed by electrophoresis in a 0.8% agarose gel. A PCR-amplified DNA fragment of the correct size (about 1.9 kb long) was electroeluted, digested with restriction enzymes NdeI and EcoRI, and subcloned into NdeI/EcoRI linearized plasmid pT7-7 to give plasmid pCD666 upon ligation and transformation into *E. coli* DH5-alpha cells. Finally, plasmid pCD666 was introduced into *E. coli* strain C600 carrying plasmid pGP1-2 (the plasmid containing the T7 RNA polymerase gene) (see Tabor, 1990). One transformant was selected for further work and recorded as strain CD673.

C. Construction of pCD736 carrying the *S. avermitilis* E1-alpha and E1-beta bkd ORFs About 2 µg of plasmid pCD670 was linearized by a partial BamHI digestion. To obtain the linear form of plasmid pCD670 aliquots of the BamHI digestion mixture were taken at the following time points: 1, 3, 5, 10, and 20 minutes. Aliquots were run through a 0.8% agarose gel. The linear form (about 4.3 kb long) was recovered by electroelution and dephosphorylated using CIAP (as described before). Then, half of the dephosphorylated linear form of plasmid pCD670 was ligated with a 0.8 kb BamHI/BglII fragment isolated from plasmid pCD577. The ligation mixture was used to transform competent *E. coli* DH5-alpha cells. Ten clones were recovered and analyzed by restriction analysis of plasmid DNA prepared by the miniprep procedure. One clone, recorded as strain CD736, contained the correctly assembled plasmid pCD736). Finally, plasmid pCD736 was introduced into *E. coli* strain C600 carrying plasmid pGP1-2. One transformant was selected for further work and recorded as strain CD737. Another clone, recorded as strain CD705, contained plasmid pCD705, which carried the 0.8 kb BamHI/BglII fragment in the wrong orientation. Construct pCD705 was used as a negative control in expression experiments.

D. Construction of pCD685 carrying the *S. avermitilis* bkd gene cluster

The remaining half of the dephosphorylated linear form of plasmid pCD670 obtained, as described above, by a partied digestion with the restriction enzyme BamHI, was ligated with a 7 kb BamHI fragment isolated from plasmid pCD577. The ligation mixture was used to transform competent *E. coli* DH5-alpha cells. Many clones were recovered and 16 of them were selected for further analysis. Plasmid DNA were extracted and analyzed by restriction analysis. One clone, recorded as strain CD685, contained the correctly assembled plasmid (pCD685). Finally, plasmid pCD685 was introduced into *E. coli* strain C600 carrying plasmid pGP1-2. One transformant was selected for further work and recorded as strain CD687.

Example 10

Expression in *Escherichia coli* of the *S. avermitilis* bkd genes by using the T7 dual plasmid system Derivatives of *E. coli* C600 (pGP-1) containing the different pT7-7 constructions (strains CD676, CD673, CD737, and CD687) were grown in 5 ml LB medium containing both kanamycin (60 µg/ml) and ampicillin (60 µg/ml) overnight at 30° C. The overnight cultures were then diluted 1:40 (0.25:10.00 ml) into a tube culture (25×150 mm) containing fresh LB/ampicillin/kanamycin medium and grown with shaker aeration at 30° C. to a measured optical density ($OD_{590}$) of about 0.4. The gene for T7 RNA polymerase was induced by raising the temperature to 42° C. for 30 minutes, which in turn induced the gone(s) under the control of the T7 promoter (as described by S. Tabor, 1990). Finally, the temperature was reduced to 37° C. and cells were grown for additional 90 minutes with shaking. Uninduced control cultures were always kept at 30° C. Proteins were analyzed by Sodium Dodecyl Sulfate (SDS) polyacrylamide gel electrophoresis as described by C. D. Denoya et al., 1986, J. Bacteriol., 168:1133–1141. Enzymatic activity was analyzed as described in Example 11.

Example 11

Determination of E1 S. *avermitilis* BCKDH Activity in Crude Extracts of Recombinant E. *coli* Strains

A. Cell Lysate Preparation

Cells (derived from 8-ml cultures) were collected by centrifugation (5 min at 5,000 rpm –3,000×g–, using a Sorvall SS-34 rotor refrigerated at 4° C.), and resuspended in 5 ml "breakage buffer" (0.05M potassium phosphate buffer, pH 7.0, containing 3% Triton X-100, 15% glycerol, 3 mM dithiothreitol, 1 mg/ml turkey egg white trypsin inhibitor, 5 mM EDTA, and 0.04 mM TPP [thiamin pyrophosphate]). Resuspended cells were transferred to a French press and the cells were ruptured by one passage at 5,000×psi. A 1.5-ml aliquot of the French pressate was then transferred to a microcentrifuge tube and clarified by 30 seconds of centrifugation at 14,000 rpm. Aliquots of 100 μl of each supernatant were used per enzyme assay. Protein concentration was determined by using the Bio-Rad protein assay (Bio-Rad Laboratories, Richmond, Calif.), which is based on the Bradford dye-binding procedure (Bradford, M., Anal. Biochem., 72:248, 1976).

B. Assay for E1 Component of the S. *avermitilis* Branched-Chain Alpha-Ketoacid Dehydrofienase (BCKDH) Complex BCKDH E1 activity was determined by a modified version of the radiochemical assay described previously (Chuang, D. T., 1988, Methods Enzymol., 166:146–154; and Hafner, E. W. et al., 1991, J. Antibiotics, 44:349). To the bottom of a 15-ml glass scintillation vial were added: 0.148 ml of 0.25M potassium phosphate buffer, pH 6.5; 0.002 ml of 0.1M ethylenediaminetetraacetic acid (EDTA, disodium salt); 0.004 ml of 0.1M $MgCl_2$; 0.02 ml of 3.7 mM thiamin pyrophosphate (TPP); 0.02 ml of 37 mM $NaAsO_2$; 0.01 ml of 37 mM 2,6-dichlorophenolindophenol (sodium salt, Sigma D-1878); 0.008 ml of alpha-[1-$^{4}$C] ketoisocaproate stock solution (prepared as described later); 0.058 ml water; and 0.1 ml of clarified cell-free extract. The mouth of the vial was immediately covered with Whatman 4CHR paper (Whatman catalog number 3004614) that has been impregnated with Solvable (a tissue and gel solubilizer purchased from NEN-Dupont). A plastic cap was then firmly placed on the vial, both the cap and the upper half of the vial were wrapped with parafilm, and incubated with gentle shaking for 2 hours at 30° C. At the completion of the incubation, the filter paper was transferred to a 7 ml glass scintillation vial containing 4 ml "Ready Safe" (Beckman) liquid scintillation cocktail to determine radioactivity. The alpha-[1-$^{14}$C] ketoisocaproate stock solution was prepared by mixing 5.6 microliters of 20 mM alpha-ketoisocaproate (sodium salt, Sigma K-0629), 50 microliters of alpha-[1-$^{14}$C] ketoisocaproate (55 mCi/mmol, 50 μCi/ml, Amersham), and enough water to a final volume of 1 ml. The specific activity of the E1 component of the branched-chain alpha-ketoacid dehydrogenase is picomoles of carbon dioxide evolved per minute per milligram of protein as shown in Table I below.

TABLE 1

E1 *Streptomyces avermitilis* branched-chain alpha-ketoacid dehydrogenase activity in crude extracts of recombinant E. *coli* cells.

| Construction | Plasmid | Strain | Induction | E1 BCKDH specific activity[1,2] |
|---|---|---|---|---|
| No Insert | pT7-7 | CD677 | + | 0.9 |
| E1 – a | pCD670 | CD676 | – | 0.6 |
|  |  |  | + | 0.8 |
| E1 – b | pCD666 | CD673 | – | 0.5 |
|  |  |  | + | 0.7 |
| E1 – [a + b] | pCD736 | CD737 | – | 2.0 |
|  |  |  | + | 13.7 |
| E1 – [a + b][3] | pCD705 | CD705 | – | 0.9 |
|  |  |  | + | 0.5 |
| E1 – [a + b] – E2 – E3 | pCD685 | CD687 | – | 2.9 |
|  |  |  | + | 6.0 |

[1]The specific activity of the E1 component of the branched-chain alpha-ketoacid dehydrogenase is picomoles of $CO_2$ evolved per minute per milligram of protein.
[2]The results are the means of duplicate determinations.
[3]This construct carries the C-terminal part of the E1-beta open reading frame in the wrong orientation and it was used as a negative control.

DESCRIPTION OF SEQUENCE ID'S

SEQUENCE ID NO. 1 represents the DNA sequence that encodes the E1-alpha subunit of S. *avermitilis* BCKDH. This sequence is also depicted in FIG. 4 as bases 403–1548.

SEQUENCE ID NO. 2 represents the DNA sequence that encodes the E1-beta subunit of S. *avermitilis* BCKDH. This sequence is also depicted in FIG. 4 as bases 1622–2626.

SEQUENCE ID NO. 3 represents the DNA sequence that begins the open reading frame that encodes the amino terminal region of the E2 subunit of S. *avermitilis* BCKDH. This sequence is also depicted in FIG. 4 as bases 2626–2727.

SEQUENCE ID NO. 4 is a DNA sequence representing bases 3–251 of pCD539. This is a partial internal sequence of the gene encoding for E2 subunit of S. *avermitilis* BCKDH. This sequence is also depicted in FIG. 5.

SEQUENCE ID NO. 5 represents the 2728 base pairs of the S. *avermitilis* genomic DNA fragment that is depicted in FIG. 4 and contains open reading frames of the E1-alpha, E1-beta and E2 (partial) subunits of S. *avermitilis* BCKDH.

SEQUENCE ID NO. 6 represents the amino acid sequence of the E1-alpha subunit of S. *avermitilis* BCKDH. This amino acid sequence is encoded by the DNA sequence of SEQUENCE ID NO. 1.

SEQUENCE ID NO. 7 represents the amino acid sequence of the E1-beta subunit of S. *avermitilis* BCKDH. This amino acid sequence is encoded by the DNA sequence of SEQUENCE ID NO. 2.

SEQUENCE ID NO. 8 represents the amino acid sequence of the amino terminal part of the E2 subunit of S. *avermitilis* BCKDH. This amino acid sequence is encoded by the DNA sequence of SEQUENCE ID NO. 3.

SEQUENCE ID NO. 9 represents the amino acid sequence encoded by the DNA sequence represented by bases 3–251 of pCD539 (SEQUENCE ID NO. 4). This amino acid sequence represents an internal peptide fragment of the E2 subunit of S. *avermitilis* BCKDH.

I claim:

1. A polypeptide consisting of the amino acid sequence of SEQUENCE ID NO. 6, SEQUENCE ID NO. 7, SEQUENCE ID NO. 8 or SEQUENCE ID NO. 9.

2. A polypeptide produced by expression in a host cell of a DNA segment that comprises the DNA sequence of SEQUENCE ID NO. 1, SEQUENCE ID NO. 2, SEQUENCE ID NO. 3, SEQUENCE ID NO. 4 or SEQUENCE ID. NO. 5.

* * * * *

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 1146 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:1:

| | | | | | | |
|---|---|---|---|---|---|---|
| ATGACGGTCA | TGGAGCAGCG | GGGCGCTTAC | CGGCCCACAC | CGCCGCCCGC | CTGGCAGCCC | 60 |
| CGCACCGACC | CCGCGCCACT | GCTGCCCGAC | GCGCTGCCCC | ACCGCGTCCT | GGGCACCGAG | 120 |
| GCGGCCGCGG | AGGCCGACCC | GCTACTGCTG | CGCCGCCTGT | ACGCGGAGCT | GGTGCGCGGC | 180 |
| CGCCGCTACA | ACACGCAGGC | CACGGCTCTC | ACCAAGCAGG | GCCGGCTCGC | CGTCTACCCG | 240 |
| TCGAGCACGG | GCCAGGAGGC | CTGCGAGGTC | GCCGCCGCGC | TCGTGCTGGA | GGAGCGCGAC | 300 |
| TGGCTCTTCC | CCAGCTACCG | GGACACCCTC | GCCGCCGTCG | CCCGCGGCCT | CGATCCCGTC | 360 |
| CAGGCGCTCA | CCCTCCTGCG | CGGCGACTGG | CACACCGGGT | ACGACCCCCG | TGAGCACCGC | 420 |
| ATCGCGCCCC | TGTGCACCCC | TCTCGCGACC | CAGCTCCCGC | ACGCCGTCGG | CCTCGCGCAC | 480 |
| GCCGCCCGCC | TCAAGGGCGA | CGACGTGGTC | GCGCTCGCCC | TGGTCGGCGA | CGGCGGCACC | 540 |
| AGCGAGGGCG | ACTTCCACGA | GGCACTGAAC | TTCGCCGCCG | TCTGGCAGGC | GCCGGTCGTC | 600 |
| TTCCTCGTGC | AGAACAACGG | CTTCGCCATC | TCCGTCCCGC | TCGCCAAGCA | GACCGCCGCC | 660 |
| CCGTCGCTGG | CCCACAAGGC | CGTCGGCTAC | GGGATGCCGG | GCCGCCTGGT | CGACGGCAAC | 720 |
| GACGCGGCGG | CCGTGCACGA | GGTCCTCAGC | GACGCCGTGG | CCCACGCGCG | CGCGGGAGGG | 780 |
| GGGCCGACGC | TCGTGGAGGC | GGTGACCTAC | CGCATCGACG | CCCACACCAA | CGCCGACGAC | 840 |
| GCGACGCGCT | ACCGGGGGGA | CTCCGAGGTG | GAGGCCTGGC | GCGCGCACGA | CCCGATCGCG | 900 |
| CTCCTGGAGC | ACGAGTTGAC | CGAACGCGGG | CTGCTCGACG | AGGACGGCAT | CCGGGCCGCC | 960 |
| CGCGAGGACG | CCGAGGCGAT | GGCCGCGGAC | CTGCGCGCAC | GCATGAACCA | GGATCCGGCC | 1020 |
| CTGGACCCCA | TGGACCTGTT | CGCCCATGTG | TATGCCGAGC | CCACCCCCCA | GCTGCGGGAG | 1080 |
| CAGGAAGCCC | AGTTGCGGGC | CGAGCTGGCA | GCGGAGGCCG | ACGGGCCCCA | AGGAGTCGGC | 1140 |
| CGATGA | | | | | | 1146 |

( 2 ) INFORMATION FOR SEQ ID NO:2:

( i ) SEQUENCE CHARACTERISTICS:
        ( A ) LENGTH: 1005 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:2:

| | | | | | | |
|---|---|---|---|---|---|---|
| ATGACCACCG | TTGCCCTCAA | GCCGGCCACC | ATGGCGCAGG | CACTCACACG | CGCGTTGCGT | 60 |
| GACGCCATGG | CCGCCGACCC | CGCCGTCCAC | GTGATGGGCG | AGGACGTCGG | CACGCTCGGC | 120 |
| GGGGTCTTCC | GGGTCACCGA | CGGGCTCGCC | AAGGAGTTCG | GCGAGGACCG | CTGCACGGAC | 180 |
| ACGCCGCTCG | CCGAGGCAGG | CATCCTCGGC | ACGGCCGTCG | GCATGGCGAT | GTACGGGCTG | 240 |

```
CGGCCGGTCG TCGAGATGCA GTTCGACGCG TTCGCGTACC CGGCGTTCGA GCAGCTCATC    300

AGCCATGTCG CGCGGGATGC GCAACGCACC CGCGGGGCGA TGCCGCTGCC GATCACCATC    360

CGTGTCCCCT ACGGCGGCGG AATCGGCGGA GTCGAACACC ACAGCGACTC CTCCGAGGCG    420

TACTACATGG CGACTCCGGG GCTCCATGTC GTCACGCCCG CCACGGTCGC CGACGCGTAC    480

GGGCTGCTGC GCGCCGCCAT CGCCTCCGAC GACCCGGTCG TCTTCCTGGA GCCCAAGCGG    540

CTGTACTGGT CGAAGGACTC CTGGAACCCG GACGAGCCGG GGACCGTTGA ACCGATAGGC    600

CGCGCGGTGG TGCGGCGCTC GGGCCGGAGC GCCACGCTCA TCACGTACGG GCCTTCCCTG    660

CCCGTCTGCC TGGAGGCGGC CGAGGCGGCC CGGGCCGAGG GCTGGGACCT CGAAGTCGTC    720

GATCTGCGCT CCCTGGTGCC CTTCGACGAC GAGACGGTTG TGCGCGTCGG TGCGCGGACC    780

GGACGCGCCG TCGTCGTGCA CGAGTCGGGT GGTTACGGCG GCCCGGGCGG GGAGATCGCC    840

GCGGGCATCA CCGAGCGCTG CTTCCACCAT CTGGAGGCGC CGGTGCTGCG CGTCGCCGGG    900

TTCGACATCC CGTATCCGCC GCCGATGCTG GAGCGCCATC ATCTGCCCGG TGTCGACCGG    960

ATCCTGGACG CGGTGGGGCG GCTTCAGTGG GAGGCGGGGA GCTGA               1005

(2) INFORMATION FOR SEQ ID NO:3:

(i) SEQUENCE CHARACTERISTICS:
        (A) LENGTH: 102 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:3:

ATGGCCCAGG TGCTCGAGTT CAAGCTCCCC GACCTCGGGG AGGGCCTGAC CGAGGCCGAG     60

ATCGTCCGCT GGCTGGTGCA GGTCGGCGAC GTCGTGGCGA TC                       102

(2) INFORMATION FOR SEQ ID NO:4:

(i) SEQUENCE CHARACTERISTICS:
        (A) LENGTH: 249 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:4:

ATCTCCCTCA TCGCGCTGCT CGCCAGGATC TGCACCGCCG CACTGGCCCG CTTCCCCGAG     60

CTCAACTCCA CCGTCGACAT GGACGCCCGC GAGGTCGTAC GGCTCGACCA GGTGCACCTG    120

GGCTTCGCCG CGCAGACCGA ACGGGGCTC GTCGTCCCGG TCGTGCGGGA CGCGCACGCG    180

CGGGACGCCG AGTCGCTCAG CGCCGAGTTC GCGCGGCTGA CCGAGGCCGC CCGGACCGGC    240

ACCCTCACA                                                           249

(2) INFORMATION FOR SEQ ID NO:5:

(i) SEQUENCE CHARACTERISTICS:
        (A) LENGTH: 2728 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:5:
```

| | | | | | | |
|---|---|---|---|---|---|---|
| GTCGACGCGG | GCTCCGAAAC | CGCGGATCAC | GCCGTCGTCG | ATGAGCCGGT | TGATTCGCGC | 60 |
| GTAGGCATTG | GCACGCGACA | CGTGGGCGCG | CTCGGCCACG | GACCGTATCG | AGGCGCGGCC | 120 |
| GTCCGCCTGG | AGCATCTGGA | GGATGTCCTG | ATCGATGGCG | TCCAGCGGGC | GGGCGGGCGG | 180 |
| CAGGGGTACC | CCGGGCTCCG | CTCCCTCGGC | CATTTGTTCA | GGTGCCATGT | CCTCCGGCCT | 240 |
| CCTTACCATG | GACGTAGTGC | GTTCATTCCA | GGCTGTGGAG | AACCGTTTGT | CCACAGCCTG | 300 |
| ACGGTGCCTG | TAGCCAAAAT | GTGCCGACGA | CCGAACAATC | GGTAGGTGAG | CGCCTCACA | 360 |
| CCCGTGGCGC | GCCCAAAGCC | GCTCCCACGA | GGAGGTGCCG | TCATGACGGT | CATGGAGCAG | 420 |
| CGGGGCGCTT | ACCGGCCCAC | ACCGCCGCCC | GCCTGGCAGC | CCCGCACCGA | CCCCGCGCCA | 480 |
| CTGCTGCCCG | ACGCGCTGCC | CCACCGCGTC | CTGGGCACCG | AGGCGGCCGC | GGAGGCCGAC | 540 |
| CCGCTACTGC | TGCGCCGCCT | GTACGCGGAG | CTGGTGCGCG | GCCGCCGCTA | CAACACGCAG | 600 |
| GCCACGGCTC | TCACCAAGCA | GGGCCGGCTC | GCCGTCTACC | CGTCGAGCAC | GGGCCAGGAG | 660 |
| GCCTGCGAGG | TCGCCGCCGC | GCTCGTGCTG | GAGGAGCGCG | ACTGGCTCTT | CCCCAGCTAC | 720 |
| CGGGACACCC | TCGCCGCCGT | CGCCCGCGGC | CTCGATCCCG | TCCAGGCGCT | CACCCTCCTG | 780 |
| CGCGGCGACT | GGCACACCGG | GTACGACCCC | CGTGAGCACC | GCATCGCGCC | CCTGTGCACC | 840 |
| CCTCTCGCGA | CCCAGCTCCC | GCACGCCGTC | GGCCTCGCGC | ACGCCGCCCG | CCTCAAGGGC | 900 |
| GACGACGTGG | TCGCGCTCGC | CCTGGTCGGC | GACGGCGGCA | CCAGCGAGGG | CGACTTCCAC | 960 |
| GAGGCACTGA | ACTTCGCCGC | CGTCTGGCAG | GCGCCGGTCG | TCTTCCTCGT | GCAGAACAAC | 1020 |
| GGCTTCGCCA | TCTCCGTCCC | GCTCGCCAAG | CAGACCGCCG | CCCCGTCGCT | GGCCCACAAG | 1080 |
| GCCGTCGGCT | ACGGGATGCC | GGGCCGCCTG | GTCGACGGCA | ACGACGCGGC | GGCCGTGCAC | 1140 |
| GAGGTCCTCA | GCGACGCCGT | GGCCCACGCG | CGCGCGGGAG | GGGGCCGAC | GCTCGTGGAG | 1200 |
| GCGGTGACCT | ACCGCATCGA | CGCCCACACC | AACGCCGACG | ACGCGACGCG | CTACCGGGGG | 1260 |
| GACTCCGAGG | TGGAGGCCTG | GCGCGCGCAC | GACCCGATCG | CGCTCCTGGA | GCACGAGTTG | 1320 |
| ACCGAACGCG | GGCTGCTCGA | CGAGGACGGC | ATCCGGGCCG | CCCGCGAGGA | CGCCGAGGCG | 1380 |
| ATGGCCGCGG | ACCTGCGCGC | ACGCATGAAC | CAGGATCCGG | CCCTGGACCC | CATGGACCTG | 1440 |
| TTCGCCCATG | TGTATGCCGA | GCCCACCCCC | CAGCTGCGGG | AGCAGGAAGC | CCAGTTGCGG | 1500 |
| GCCGAGCTGG | CAGCGGAGGC | CGACGGGCCC | CAAGGAGTCG | GCCGATGAAG | AGAGTTGACC | 1560 |
| ATCGGGCCCC | GAGAAGCGGG | CCGATGACCT | CCGTTGGCCT | TTGGCCGGAA | GGAGCCGGGC | 1620 |
| GATGACCACC | GTTGCCCTCA | AGCCGGCCAC | CATGGCGCAG | GCACTCACAC | GCGCGTTGCG | 1680 |
| TGACGCCATG | GCCGCCGACC | CCGCCGTCCA | CGTGATGGGC | GAGGACGTCG | GCACGCTCGG | 1740 |
| CGGGGTCTTC | CGGGTCACCG | ACGGGCTCGC | CAAGGAGTTC | GGCGAGGACC | GCTGCACGGA | 1800 |
| CACGCCGCTC | GCCGAGGCAG | GCATCCTCGG | CACGGCCGTC | GGCATGGCGA | TGTACGGGCT | 1860 |
| GCGGCCGGTC | GTCGAGATGC | AGTTCGACGC | GTTCGCGTAC | CCGGCGTTCG | AGCAGCTCAT | 1920 |
| CAGCCATGTC | GCGCGGGATG | CGCAACGCAC | CCGCGGGGCG | ATGCCGCTGC | CGATCACCAT | 1980 |
| CCGTGTCCCC | TACGGCGGCG | GAATCGGCGG | AGTCGAACAC | CACAGCGACT | CCTCCGAGGC | 2040 |
| GTACTACATG | GCGACTCCGG | GGCTCCATGT | CGTCACGCCC | GCCACGGTCG | CCGACGCGTA | 2100 |
| CGGGCTGCTG | CGCGCCGCCA | TCGCCTCCGA | CGACCGGTC | GTCTTCCTGG | AGCCCAAGCG | 2160 |
| GCTGTACTGG | TCGAAGGACT | CCTGGAACCC | GGACGAGCCG | GGGACCGTTG | AACCGATAGG | 2220 |
| CCGCGCGGTG | GTGCGGCGCT | CGGGCCGGAG | CGCCACGCTC | ATCACGTACG | GGCCTTCCCT | 2280 |
| GCCCGTCTGC | CTGGAGGCGG | CCGAGGCGGC | CCGGGCCGAG | GGCTGGGACC | TCGAAGTCGT | 2340 |
| CGATCTGCGC | TCCCTGGTGC | CCTTCGACGA | CGAGACGGTT | GTGCGCGTCG | GTGCGCGGAC | 2400 |

```
CGGACGCGCC  GTCGTCGTGC  ACGAGTCGGG  TGGTTACGGC  GGCCCGGGCG  GGGAGATCGC        2460

CGCGGGCATC  ACCGAGCGCT  GCTTCCACCA  TCTGGAGGCG  CCGGTGCTGC  GCGTCGCCGG        2520

GTTCGACATC  CCGTATCCGC  CGCCGATGCT  GGAGCGCCAT  CATCTGCCCG  GTGTCGACCG        2580

GATCCTGGAC  GCGGTGGGGC  GGCTTCAGTG  GGAGGCGGGG  AGCTGATGGC  CCAGGTGCTC        2640

GAGTTCAAGC  TCCCCGACCT  CGGGGAGGGC  CTGACCGAGG  CCGAGATCGT  CCGCTGGCTG        2700

GTGCAGGTCG  GCGACGTCGT  GGCGATCG                                              2728
```

( 2 ) INFORMATION FOR SEQ ID NO:6:

( i ) SEQUENCE CHARACTERISTICS:
        ( A ) LENGTH: 381 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
Met Thr Val Met Glu Gln Arg Gly Ala Tyr Arg Pro Thr Pro Pro Pro
  1               5                  10                  15

Ala Trp Gln Pro Arg Thr Asp Pro Ala Pro Leu Leu Pro Asp Ala Leu
             20                  25                  30

Pro His Arg Val Leu Gly Thr Glu Ala Ala Glu Ala Asp Pro Leu
         35                  40                  45

Leu Leu Arg Arg Leu Tyr Ala Glu Leu Val Arg Gly Arg Arg Tyr Asn
     50                  55                  60

Thr Gln Ala Thr Ala Leu Thr Lys Gln Gly Arg Leu Ala Val Tyr Pro
 65                  70                  75                  80

Ser Ser Thr Gly Gln Glu Ala Cys Glu Val Ala Ala Ala Leu Val Leu
                 85                  90                  95

Glu Glu Arg Asp Trp Leu Phe Pro Ser Tyr Arg Asp Thr Leu Ala Ala
            100                 105                 110

Val Ala Arg Gly Leu Asp Pro Val Gln Ala Leu Thr Leu Leu Arg Gly
            115                 120                 125

Asp Trp His Thr Gly Tyr Asp Pro Arg Glu His Arg Ile Ala Pro Leu
    130                 135                 140

Cys Thr Pro Leu Ala Thr Gln Leu Pro His Ala Val Gly Leu Ala His
145                 150                 155                 160

Ala Ala Arg Leu Lys Gly Asp Asp Val Val Ala Leu Ala Leu Val Gly
                165                 170                 175

Asp Gly Gly Thr Ser Glu Gly Asp Phe His Glu Ala Leu Asn Phe Ala
            180                 185                 190

Ala Val Trp Gln Ala Pro Val Val Phe Leu Val Gln Asn Asn Gly Phe
        195                 200                 205

Ala Ile Ser Val Pro Leu Ala Lys Gln Thr Ala Ala Pro Ser Leu Ala
    210                 215                 220

His Lys Ala Val Gly Tyr Gly Met Pro Gly Arg Leu Val Asp Gly Asn
225                 230                 235                 240

Asp Ala Ala Ala Val His Glu Val Leu Ser Asp Ala Val Ala His Ala
                245                 250                 255

Arg Ala Gly Gly Gly Pro Thr Leu Val Glu Ala Val Thr Tyr Arg Ile
            260                 265                 270

Asp Ala His Thr Asn Ala Asp Asp Ala Thr Arg Tyr Arg Gly Asp Ser
        275                 280                 285

Glu Val Glu Ala Trp Arg Ala His Asp Pro Ile Ala Leu Leu Glu His
```

|     |     |     |     |     | 290 |     |     |     |     | 295 |     |     |     |     | 300 |     |     |     |     |
|-----|-----|-----|-----|-----|-----|-----|-----|-----|-----|-----|-----|-----|-----|-----|-----|-----|-----|-----|-----|
| Glu | Leu | Thr | Glu | Arg | Gly | Leu | Leu | Asp | Glu | Asp | Gly | Ile | Arg | Ala | Ala |
| 305 |     |     |     |     | 310 |     |     |     |     | 315 |     |     |     |     | 320 |
| Arg | Glu | Asp | Ala | Glu | Ala | Met | Ala | Ala | Asp | Leu | Arg | Ala | Arg | Met | Asn |
|     |     |     |     | 325 |     |     |     |     | 330 |     |     |     |     | 335 |     |
| Gln | Asp | Pro | Ala | Leu | Asp | Pro | Met | Asp | Leu | Phe | Ala | His | Val | Tyr | Ala |
|     |     |     | 340 |     |     |     | 345 |     |     |     |     | 350 |     |     |     |
| Glu | Pro | Thr | Pro | Gln | Leu | Arg | Glu | Gln | Glu | Ala | Gln | Leu | Arg | Ala | Glu |
|     |     | 355 |     |     |     |     | 360 |     |     |     |     | 365 |     |     |     |
| Leu | Ala | Ala | Glu | Ala | Asp | Gly | Pro | Gln | Gly | Val | Gly | Arg |
|     | 370 |     |     |     | 375 |     |     |     |     | 380 |     |     |

(2) INFORMATION FOR SEQ ID NO:7:

(i) SEQUENCE CHARACTERISTICS:
    (A) LENGTH: 334 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:7:

| Met | Thr | Thr | Val | Ala | Leu | Lys | Pro | Ala | Thr | Met | Ala | Gln | Ala | Leu | Thr |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Arg | Ala | Leu | Arg | Asp | Ala | Met | Ala | Ala | Asp | Pro | Ala | Val | His | Val | Met |
|     |     |     | 20  |     |     |     |     | 25  |     |     |     |     | 30  |     |     |
| Gly | Glu | Asp | Val | Gly | Thr | Leu | Gly | Gly | Val | Phe | Arg | Val | Thr | Asp | Gly |
|     |     | 35  |     |     |     |     | 40  |     |     |     |     | 45  |     |     |     |
| Leu | Ala | Lys | Glu | Phe | Gly | Glu | Asp | Arg | Cys | Thr | Asp | Thr | Pro | Leu | Ala |
|     | 50  |     |     |     |     | 55  |     |     |     |     | 60  |     |     |     |     |
| Glu | Ala | Gly | Ile | Leu | Gly | Thr | Ala | Val | Gly | Met | Ala | Met | Tyr | Gly | Leu |
| 65  |     |     |     |     | 70  |     |     |     |     | 75  |     |     |     |     | 80  |
| Arg | Pro | Val | Val | Glu | Met | Gln | Phe | Asp | Ala | Phe | Ala | Tyr | Pro | Ala | Phe |
|     |     |     |     | 85  |     |     |     |     | 90  |     |     |     |     | 95  |     |
| Glu | Gln | Leu | Ile | Ser | His | Val | Ala | Arg | Asp | Ala | Gln | Arg | Thr | Arg | Gly |
|     |     |     | 100 |     |     |     |     | 105 |     |     |     |     | 110 |     |     |
| Ala | Met | Pro | Leu | Pro | Ile | Thr | Ile | Arg | Val | Pro | Tyr | Gly | Gly | Gly | Ile |
|     |     | 115 |     |     |     |     | 120 |     |     |     |     | 125 |     |     |     |
| Gly | Gly | Val | Glu | His | His | Ser | Asp | Ser | Ser | Glu | Ala | Tyr | Tyr | Met | Ala |
|     | 130 |     |     |     |     | 135 |     |     |     |     | 140 |     |     |     |     |
| Thr | Pro | Gly | Leu | His | Val | Val | Thr | Pro | Ala | Thr | Val | Ala | Asp | Ala | Tyr |
| 145 |     |     |     |     | 150 |     |     |     |     | 155 |     |     |     |     | 160 |
| Gly | Leu | Leu | Arg | Ala | Ile | Ala | Ser | Asp | Asp | Pro | Val | Val | Phe | Leu |
|     |     |     |     | 165 |     |     |     |     | 170 |     |     |     |     | 175 |     |
| Glu | Pro | Lys | Arg | Leu | Tyr | Trp | Ser | Lys | Asp | Ser | Trp | Asn | Pro | Asp | Glu |
|     |     |     | 180 |     |     |     |     | 185 |     |     |     |     | 190 |     |     |
| Pro | Gly | Thr | Val | Glu | Pro | Ile | Gly | Arg | Ala | Val | Val | Arg | Arg | Ser | Gly |
|     |     | 195 |     |     |     |     | 200 |     |     |     |     | 205 |     |     |     |
| Arg | Ser | Ala | Thr | Leu | Ile | Thr | Tyr | Gly | Pro | Ser | Leu | Pro | Val | Cys | Leu |
|     | 210 |     |     |     |     | 215 |     |     |     |     | 220 |     |     |     |     |
| Glu | Ala | Ala | Glu | Ala | Ala | Arg | Ala | Glu | Gly | Trp | Asp | Leu | Glu | Val | Val |
| 225 |     |     |     |     | 230 |     |     |     |     | 235 |     |     |     |     | 240 |
| Asp | Leu | Arg | Ser | Leu | Val | Pro | Phe | Asp | Asp | Glu | Thr | Val | Val | Arg | Val |
|     |     |     |     | 245 |     |     |     |     | 250 |     |     |     |     | 255 |     |
| Gly | Ala | Arg | Thr | Gly | Arg | Ala | Val | Val | Val | His | Glu | Ser | Gly | Gly | Tyr |
|     |     |     | 260 |     |     |     |     | 265 |     |     |     |     | 270 |     |     |

```
Gly Gly Pro Gly Gly Glu Ile Ala Ala Gly Ile Thr Glu Arg Cys Phe
        275                 280                 285

His His Leu Glu Ala Pro Val Leu Arg Val Ala Gly Phe Asp Ile Pro
    290                 295                 300

Tyr Pro Pro Pro Met Leu Glu Arg His His Leu Pro Gly Val Asp Arg
305                 310                 315                 320

Ile Leu Asp Ala Val Gly Arg Leu Gln Trp Glu Ala Gly Ser
                325                 330
```

( 2 ) INFORMATION FOR SEQ ID NO:8:

( i ) SEQUENCE CHARACTERISTICS:
        ( A ) LENGTH: 34 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

```
Met Ala Gln Val Leu Glu Phe Lys Leu Pro Asp Leu Gly Glu Gly Leu
1               5                   10                  15

Thr Glu Ala Glu Ile Val Arg Trp Leu Val Gln Val Gly Asp Val Val
            20                  25                  30

Ala Ile
```

( 2 ) INFORMATION FOR SEQ ID NO:9:

( i ) SEQUENCE CHARACTERISTICS:
        ( A ) LENGTH: 83 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

```
Ile Ser Leu Ile Ala Leu Leu Ala Arg Ile Cys Thr Ala Ala Leu Ala
1               5                   10                  15

Arg Phe Pro Glu Leu Asn Ser Thr Val Asp Met Asp Ala Arg Glu Val
            20                  25                  30

Val Arg Leu Asp Gln Val His Leu Gly Phe Ala Ala Gln Thr Glu Arg
        35                  40                  45

Gly Leu Val Val Pro Val Val Arg Asp Ala His Ala Arg Asp Ala Glu
    50                  55                  60

Ser Leu Ser Ala Glu Phe Ala Arg Leu Thr Glu Ala Ala Arg Thr Gly
65                  70                  75                  80

Thr Leu Thr
```

( 2 ) INFORMATION FOR SEQ ID NO:10:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

GAATTCCGCG ACCGGCGCCA CCTCCGAGGC CGAC                      34

( 2 ) INFORMATION FOR SEQ ID NO:11:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

TCTAGACCGC AGGTGGTCCG GCATGTC                          27

( 2 ) INFORMATION FOR SEQ ID NO:12:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

AAGGATCCTG CAGCCCAGTC ACGACGTTGT AAAACGA             37

( 2 ) INFORMATION FOR SEQ ID NO:13:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:13:

AAGGATCCTG CAGACAGCTA TGACCATGAT TACGCCA             37

( 2 ) INFORMATION FOR SEQ ID NO:14:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

AAGAGATCTC ATATTTCATG GAGCAGCGG                     29

( 2 ) INFORMATION FOR SEQ ID NO:15:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:15:

AAGAGATCTC ATATGACCAC CGTTGCCCTG AAG                 33